(12) United States Patent
Stupp et al.

(10) Patent No.: US 7,745,708 B2
(45) Date of Patent: *Jun. 29, 2010

(54) SELF-ASSEMBLY OF PEPTIDE-AMPHIPHILE NANOFIBERS UNDER PHYSIOLOGICAL CONDITIONS

(75) Inventors: Samuel I. Stupp, Chicago, IL (US); Jeffrey D. Hartgerink, Pearland, TX (US); Elia Beniash, Auburndale, MA (US)

(73) Assignee: Northwestern University, Evanston, IL (US)

( * ) Notice: Subject to any disclaimer, the term of this patent is extended or adjusted under 35 U.S.C. 154(b) by 33 days.

This patent is subject to a terminal disclaimer.

(21) Appl. No.: 11/863,975

(22) Filed: Sep. 28, 2007

(65) Prior Publication Data

US 2008/0177033 A1   Jul. 24, 2008

Related U.S. Application Data

(62) Division of application No. 10/368,517, filed on Feb. 18, 2003, now Pat. No. 7,371,719.

(60) Provisional application No. 60/357,228, filed on Feb. 15, 2002.

(51) Int. Cl.
B32B 15/00 (2006.01)
A61K 38/00 (2006.01)

(52) U.S. Cl. ............... 977/705; 428/822; 428/546; 428/148; 530/350; 424/278.1

(58) Field of Classification Search .............. None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,853,830 A | 12/1998 | McCaulley et al. | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,114,038 A | 9/2000 | Castro et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,309,862 B1 | 10/2001 | Jarekrans et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2004/0001893 A1 | 1/2004 | Stupp et al. | |
| 2004/0018961 A1 | 1/2004 | Stupp et al. | |
| 2004/0022718 A1 | 2/2004 | Stupp et al. | |
| 2004/0214272 A1 | 10/2004 | La Rosa et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0247165 A1 | 11/2006 | Stupp et al. | |

FOREIGN PATENT DOCUMENTS

| JP | 403099096 A | 4/1991 |
|---|---|---|
| WO | 93/33243 A1 | 11/1993 |
| WO | 94/02506 A1 | 2/1994 |

(Continued)

OTHER PUBLICATIONS

Cui et al. (2009) Self-assembly of giant peptide nanobelts, Nano Lett., vol. 9, No. 3, pp. 945-951.*

Brown, Walter E. Dec. 15, 1962. "Octacalcium Phosphate and Hydroxyapatite." *Nature*. vol. 196, pp. 1018-1050.

Liang, W. Y. and A. D. Yoffe. Jan. 8, 1968. "Transmission Spectra of ZnO Single Crystals." *Physical Review Letters*. vol. 20, No. 2, pp. 59-62.

Greenfield, Norma and Gerald D. Fasman. Oct. 1969. "Computed Circular Dichroism Spectra for the Evaluation of Protein Conformation." *Biochemistry*. vol. 8, No. 10, pp. 4108-4116.

(Continued)

*Primary Examiner*—Anand U Desai
*Assistant Examiner*—Samuel Liu

(57) ABSTRACT

Peptide amphiphile compounds, compositions and methods for self-assembly or nanofibrous network formation under neutral or physiological conditions.

16 Claims, 19 Drawing Sheets

FOREIGN PATENT DOCUMENTS

| WO | WO 97/14713 A1 | 4/1997 |
|---|---|---|
| WO | WO 97/20639 A1 | 6/1997 |
| WO | WO 98/07752 A1 | 2/1998 |
| WO | WO 99/36107 A1 | 7/1999 |
| WO | 99/55383 A2 | 11/1999 |
| WO | WO 00/13710 A2 | 3/2000 |
| WO | 00/45831 A1 | 8/2000 |
| WO | WO 00/44808 A1 | 8/2000 |
| WO | WO 00/52145 A2 | 9/2000 |
| WO | WO 00/64481 A1 | 11/2000 |
| WO | WO 01/00650 A1 | 1/2001 |
| WO | WO 02/062969 A2 | 8/2002 |
| WO | WO 03/040336 A2 | 5/2003 |
| WO | WO 03/054146 A2 | 7/2003 |
| WO | WO 03/070749 A2 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | WO 2004/072104 A2 | 8/2004 |
| WO | 2004/091370 A2 | 10/2004 |
| WO | WO 20041106359 A2 | 12/2004 |
| WO | WO 2005/003292 A2 | 1/2005 |
| WO | 2005/014619 A2 | 2/2005 |
| WO | WO 2005/056039 A1 | 6/2005 |
| WO | WO 2005/056576 A2 | 6/2005 |
| WO | WO 2006/096614 A2 | 9/2006 |

OTHER PUBLICATIONS

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem*. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society*. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science*. vol. 195, No. 4275, pp. 302-304.

Biesecker, G., J. Ieuan Harris, J. C. Thierry, J. E. Walker, and A. J. Wonacott. Mar. 24., 1977. *Nature*. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society*. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International*. vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature*. vol. 284, pp. 264-265.

Lim, Franklin and Anthony M. Sun. Nov. 21, 1980. "Microencapsulated Islets as Bioartificial Endocrine Pancreas." *Science*. vol. 210, No. 4472, pp. 908-910.

Jain, Rakesh K., Chhitar M. Gupta, and Nitya Anand. 1981. "Synthesis of Peptidylglycophospholipids. Novel Derivatives of Muramyl-Dipeptide." *Tetrahedron Letters*. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry*. vol. 117, pp. 147- 157.

Yannas, I. V., J. F. Burke, D. P. Orgill, E. M. Skrabut. Jan. 8, 1982, "Wound Tissue Can Utilize a Polymeric Template to Synthesize a Functional Extension of Skin." *Science*. vol. 215. No. 4529, pp. 174-476.

Montesano, R., L. Orci, and P. Vassalli. Nov. 1983. "In Vitro Rapid Organization of Endothelial Cells into Capillary-like Networks Is Promoted by Collagen Ntratices." *The Journal of Cell Biology*. vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature*. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol*. vol. A 2, No. 2, pp. 1108-111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta*. vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group."*Chemistry Letters*. No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America*. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol, 206, No. 2, pp. 262-266.

Mann, Stephen, John P. Hannington, and R. J. P. Williams. Dec. 11, 1986. "Phospholipid Vesicles as a Model System the Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology*. vol. 131, pp. 123-130.

Lambert, Joseph B., Herbert F. Shurvell. David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. , vol. 9, No. 1, pp. 21-32.

Oonishi, H., M. Yamamoto, H. Ishimaru, E. Tsuji, S. Kuskitani, M. Aono, and V. Ukon. Mar. 1989. "The Effect of Hydroxyapatite Coating on Bone Growth into Porous Titanium Alloy Implants." *The Journal of Bone and Joint Surgery*. vol, 71-B, No. 2, pp. 213-216.

Friedmann, Theodore, Jun. 16, 1980. "Progress Toward Human Gene Therapy." *Science*. vol. 244, No. 4910. pp. 1275-1281.

Traub, Wolfie, Talmon Arad, and Stephen Weiner. Dec. 15, 1989, "Three-Dimensional Ordered Distribution of Crystals in Turkey Tendon Collagen Fibers." *Proceedings of the National Academy of Sciences of the United States of America*. vol. 86, No. 24. pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph. Edward F. Fritsch, and Thomas Maniatis. 1989. "Genes Encoding Selectable Markers." *Molecular Cloning: A Laboratory Manual. 2nd* ed, New York: Cold Spring Harbor Laboratory Press. pp. 16.9-16.15.

Veis, A. 1989. "Biochemical Studies of Vertebrate Tooth Mineralization." *Biomineralization*. S. Mann, J. Webb, and R. J. P. Williams, editors, Weinheim, Federal Republic of Germany: VCH Verlagsgesellschaft and New York: VCH Publishers. pp. 189-222.

Schnell, Lisa and Martin E. Schwab. Jan. 18, 1990, "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. Vol. 24, No. 1, pp. 17-23.

Van de Pol, Frans C. M. Dec. 1990. "Thin-Film ZnO—Properiies and Applications." *Ceramic Bulletin*. vol. 69, No. 12, pp.1959-1965.

Addadi, L., A. Berman, J. Moradian-Oldak, and S. Weiner. Dec. 28, 1990. "Tuning of Crystal Nucleation and Growth by Proteins: molecular interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt, 1990. "Modulation of Cell Adhesion by Modification of Titanium Surfaces with Covalently Attached Self-Assembled monolayers." *Journal of Biomedical materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry*. vol. 56, No. 22, pp. 14353-14358.

Harris, Robin, Editor. 1991. *Electron Microscopy in Biology: A Practical Approach*. New York: Oxford University Press.

Jackson, David Y., David S. King. Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Angstroms to Microns." *The FASEB Journal*. vol. 6, pp. 879-885.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activites to the All-L- Peptide in Vitro and in Vivo." The journal of Biological Chemistry. vol. 267, No. 20, pp. 14118-14121.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*, vol. 114, No. 10, pp. 4000-4002.

Kunitake, Toyoki. 1992. "Synthetic Bilayer Membranes: Molecular Design, Self-Organization, and Application," *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructrue." *Journal of Biomedical Materials Research.* vol. 26, p. 1689-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research.* vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T, Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*, vol. 150, No. 2, pp. 745-747.

Nomizu, Motoyoshi, Keizo Yamamura, Hynda K. Kleinman, Yoshihiko Yamada. Aug. 1, 1993. "Multimeric Forms of Tyr-lle-Gly-Ser-Arg (YIGSR) Peptide Enchance the Inhibition of Tumor Growth and Metastasis." *Cancer Research.* vol. 53, pp. 3459-3461.

Ross-Murphy S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Resides." *The Journal of Biological Chemistry*. vol. 268, No. 26, pp. 19228-19231.

Fowler, Bruce O., Milenko Marković, and Walter E. Brown, 1993. "Octacalcium Phosphate. 3. Infrared and Raman Vibrational Spectra." *Chem. Mater.* vol. 5, No. 10, pp. 1417-1423.

Fuhrhop, Jürgen-Hinrich, Dragan Spiroski, and Christoph Boettcher. 1993. "Molecular monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147. pp. 50-58.

Stupp, Samuel I., Jacqueline A. Hanson, Jo Ann Eurell, Glenn W. Ciegler, and Ann Johnson. 1993. "Organooapatites: Materials for Artifical Bone. III. Biological Testing." *Journal of Biomedical Materials Research*. vol. 27, pp. 301-311.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol . 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research.* vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology.* vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research.* vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials.* vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research.* vol. 28, pp. 909-917.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Mikos, Antonios G., Michelle D. Lyman, Lisa E. Freed, and Robert langer. 1994. "Wetting of Poly(L-Lactic Acid) and Poly(DL-Lactic-co-glycolicAcid) Foams for Tissue Culture." *Biomaterials.* vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance.* vol. 4, No. 3, pp. 334-345.

Hubbell, Jeffrey A. Jun. 1995. "Biomaterials in Tissue Engineering." *Bio/technology.* vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics.* vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve.* vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research.* vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society.* vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience.* vol. 18, pp. 159-192.

Jackowski, Andre. 1995. "Neural Injury Repair: Hope for the Future as Barriers to Effective CNS Regeneration Become Clearer." *J. Neurosurg.* vol. 9, pp. 303-317.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IkVaV).a" *FEBS Letters.* vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue ngineering.* vol. 1, No. 4, pp. 327-343.

Sasanuma, Michio. 1995. "Optical Processes in ZnO." *J. Phys.: Condens. Matter.* vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials.* vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science.* vol. 271, No. 5245, pp. 67-69.

Alivisatos, A. P. Feb. 16, 1996. "Semiconductor Clusters, Nanocrystals, and Quantum Dots." *Science.* vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry.* vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature.* vol. 381, pp. 56-58.

Hortelano, Gonzalo, Ayman Al-Hendy, Frederick A. Ofosu, and Patricia L. Chang. Jun. 15, 1996, "Delivery of Human Factor IX in Mice by Encapsulated Recombinant Myoblasts: A Novel Approach Towards Allogenic Gene Therapy of Hemophilia B." *Blood.* vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction," *J. Microencapsulation.* vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature.* vol. 382, pp. 609-611.

George, Anne, Leslie Bannon, Boris Sabsay, Jerry W. Dillon, James Malone, Arthur Veis, Nancy A. Jenkins, Debra; J. Gilbert, and Neal G. Copeland. Dec. 20, 1996. "Carboxyl-terminal Domain of Phosphophoryn Contains Unique Extended Triplet Amino Acid Repeat Sequences Forming Ordered Carboxyl-Phosphate Interaction Rides That May Be Essential in the Biomineralization Process." *The Journal of Biological Chemistry.* . vol.271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology.* vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun.* pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J.* vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir.* vol. 12, No. 20, 4748-4753.

Landis, William J., Karen J. Hodgens, James Arena, Min Ja Song, and Bruce F. McEwen. 1.996, "Structural Relations Between Collagen and Mineral in Bone as Determined by High Voltage Electron Microscopic Tomography." *Microscopy Research and Technique.* vol. 33, pp. 192-202.

Matsuzawa, Mieko Forrest F. Weight, Richard S. Potember, and Päivi Liesi. 1996. "Directional Neurite Outgrowth and Axonal Differentiation of Embryonic Hippocampal Neurons Are promoted by a neurite Outgrowth Domain of the B2-Chain of Laminin." *Int. J. Devl. Neuroscience.* vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials.* vol. 17, No. 14, pp. 1417-1422.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Ratner, Buddy D., Allan S. Hoffman, Frederick J. Schoen, and Jack E. Lemons, Editors. 1996. *Biomaterials Science: An Introduction to Materials in Medicine.* San Diego, CA: Academic Press.

Ulman, Abraham. 1996. "Formation and Structure of Self-Assembled Monolayers." *Chemical Reviews.* vol. 96, No. 4, pp. 1533-1554.

Yu, Ying-Ching. Peter Berndt, Matthew Tirrell, and Gregg B. Fields. 1996. "Self-Assembling Amphiphiles for Construction of Protein Molecular Architecture." *Journal of the American Chemical Society.* vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids.* vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature.* vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry.* vol. 272, No. 26, pp. 16382-16389.

Dimmeler, Stefanie and Andeas M. Zeiher, Aug. 1997. "nitric Oxide and Apoptosis: Another Paradigm for the Double-Edged Role of Nitric oxide." *Nitric Oxide: Biology and Chemistry.* vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science.* vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation.* vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem.* vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews.* vol. 28, pp. 5-24.

Draget, Kurt Ingar, Gudmund Skjåk-Bræk, Olav Smidsrod. 1997. "Alginate Based New Materials." *International Journal of Biological Macromolecules.* vol. 21, pp. 47-55.

El-Ghannam, Ahmed, Paul Ducheyne, and Irving M. Shapiro. 1997. "Porous Bioactive Glass and hydroxyapatite Ceramic Affect Bone Cell Function In Vitro Along Different Time Lines." *Journal of Biomedical Materials Research.* vol. 36, pp. 167-180.

Goveas, J. L. and S. T. Milner. 1997. "Dynamics of the Lamellar—Cylindrical Transition in Weakly Segregated Diblock Copolymer Melts." *Macromolecules.* vol. 30, No. 9, pp. 2605-2612.

Jaiswal, Neelam, Stephen E. Haynesworth, Arnold I. Caplan, and Scott P. Bruder. 1997. "Osteogenic Differentiation fo Purified, Culture-Expanded Human Mesenchymal Stem Cells In Vitro." *Journal of Cellular Biochemistry.* vol. 64, pp. 295-312.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.).* vol. 38, pp. 95-104.

Mann, Stephen. 1997. "Biomineralization: The Form(id)able Part of Bioinorganic Chemistry!" *J. Chem. Soc., Dalton Trans.* pp. 3953-3961.

Norrby, Klas. 1997. "Angiogenesis: New Aspects Relating to Its Initiation and Control." *APMIS.* vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society.* vol. 119, No. 26, pp. 6209-6210, S2-S17.

Smith, George P. and Valery A. Petrenko. 1997. "Phage Display." *Chemical Reviews.* vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters.* pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology.* vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials.* vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology.* vol. 289, pp. 571-587.

Zhitomirsky, I. and L. Gal-Or. 1997. "Electrophoretic Deposition of Hydroxyapatite." *Journal of Materials Science: Materials in Medicine.* pp. 213-219.

Veis Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences.* vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery.* vol. 42, No. 4, pp. 858-867.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science.* vol. 281, No. 5375, pp. 389-392.

Orgill, Dennis P., Charles Butler. John F. Regan, Mark S. Barlow. I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery.* vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *journal of the American Chemical Society.* vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System," *Journal of Biomedical Materials Research.* vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.).* vol. 43, pp. 380-398.

Fernandez, A., M. A. Alsina, I. Haro, R. Galantai, and F. Reig. 1998. "Synthesis and Physicochemical Characterization of Cyclic Laminin Related Peptides." *Langmuir.* vol. 14, No. 13, pp. 3625-3630.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science).* vol. 47, pp. 143-151.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998, "*In Vitro* Chondrogenesis of Bone Marrow-Derived Mesenchymal Progenitor Cells." *Experimental Cell Research.* vol. 238, pp. 265-272.

Kawasaki, M., A. Ohtomo, I. Ohkubo, H. Koinuma, Z. K. Tang;, P. Yu, G. K. L. Wong, B. P. Zhang, and Y. Segawa. 1998. "Excitonic Ultraviolet Laser Emmission at Room Temperature from Naturally Made Cavity in ZnO Nanocrytal thin Films." *Materials Science and Engineerintg.* vol. B56, pp. 239- 245.

Kogiso, Masaki, Satomi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir.* vol. 14, No. 18, pp. 4978-4986.

Kogiso, Masaki, Takeshi Hanada, Kiyoshi Yase, and Toshimi Shimizu. 1998. "Intralayer Hydrogen-Bond-Directed self-Assembly of Nano-Fibers from Dicarboxylic Valylvaline Bolaamphiphiles." *Chem. Comm.* pp. 1791-1792.

Li, Panjian and Paul Ducheyne. 1998. "Ouasi-Biological Apatite Film Induced by Titanium in a Simulated Body Fluid." *Journal of Biomedical Materials Research.* vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research.* vol. 40, pp. 324-335.

Tsui, Y. C., C. Doyle, and T. W. Clyne. 1998. "Plasma Sprayed Hydroxyapatite Coatings on Titanium Substrated Part 2: Optimisation of Coating Properties." *Biomaterials.* vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijin, F. Z. Cui, and K. de Groot. 1998. "Preparation of Calcium Phosphate Coatings on Titanium Implant Materials by Simple Chemistry." *Journal of Biomedical Materials Research.* vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.).* vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research.* vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Ssurfaces." *Langmuir.* vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society.* vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society.* vol. 120, No. 47, pp. 12192-12199.

Chusuci, Charles C., D. Wayne Goodman, Michael J. Van Stipdonk, Dina R. Justes, and Emile A Schweikert. Jan. 1, 1999. "Calcium Phosphate Phase Identification Using XPS and Time-of-Flight Cluster SIMS." *Analytical Chemistry.* vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science.* vol. 283, pp. 523-526.

Won, You-Yeon, H. Ted Davis, and Frank S. Bates. Feb. 12, 1999. "Giant Wormlike Rubber Micelles." *Science.* vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "microcontact Printing for Precise Control of Nerve Cell Growth in Culture." *Journal of Biomechanical Engineering.* vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters.* vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature.* vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science.* vol. 284, pp. 489-493.

Hahn, Jungscok and Stephen E. Webber. Apr. 1999. "Modification of Surfaces By Covalent Attachment of Polymer Micelles." *Macromolecular Symposia.* vol. 139, pp. 39-47.

Liu, Yi, Duckhyun Kim, B. Timothy Himes, Stella Y. Chow, Timothy Schallert Marison Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *the Journal of Neuroscience.* vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology.* Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine.* vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation," *Chem. Mater.* vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin.* vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery.* vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine.* vol. 10, pp. 465-469.

Clark, Thomas D., Kenji Kobayashi, and M. Reza Chadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Copper, and I. R. Reid. 1999. "Trifluoroacetate, a Contaminant in Purified Proteins, Inhibits Proliferation of Osteoblasts and Chondrocytes." *Am. J. Physiol. Endorinol. Metab.* vol. 277, pp. 779-783.

Emoto, Kazunori, Yukio nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir.* vol. 15, No. 16, pp. 5212-5218.

Fields, Gregg B. 1999. "Induction of Protein-like Molecular Architecture by Self-Assembly Processes." *Bioorganic & Medicinal Chemistry.* vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and Its Receptor Tie-2 Participate in the Regulation of Capillary-like tubule Formation and survival of Endothelial Cells." *microvascular Research.* vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research.* vol. 47, pp. 504-515.

Ignjatović, Nenad, Simonida Tomićć, Momčilo Dakić, Miroslav Miljlović, Milenko Plavšić, and Dragan Uskoković. 1999. "Synthesis and Properties of Hydroxyapatite/Poly-L-Lactide Composite Biomaterials." *Biomaterials.* vol. 20, pp. 809-816.

Lee, Kevin J. and Thomas M. Jessel. 1999. "The Specification of Dorsal Cell Fates in the Vertebrate Central Nervous System." *Annual Review of Neuroscience.* vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir.* vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth.* vol. 206, pp. 308-321.

lvliyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials.* vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials.* vol. 20, pp. 2265-2279.

Pittenger, Mark F., Alastair M. Mackay, Stephen C. Beck, Rama K. Jaiswal, Robin Douglas, Joseph D. Mosea, Mark A. Moorrman, Donald W. Simonetti, Stewart Craig, and Daniel R. Marshak. Apr. 2, 1999. "Multilineage Potential of Adult Human Mesenchymal Stem Cells." *Science.* vol. 284, pp. 143-147.

Rezania, Alireza, Robert Johnson, Anthony R. Lefkow, and Kevin E. Healy. 1999. "Bioactivation of Metal Oxide Surfaces. 1. Surface Charcterization and Cell Response." *Langmuir.* vol, 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials.* vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem.* vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine.* vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research.* vol. 57, pp. 188-133.

Wei, M., A. J. Ruys, M. V. Swain, S. H. Kim, B. K. Milthorpe, and C. C. Sorrell, 1999. "Interfacial Bond Strength of Electrophoretically Deposited Hydroxyapatite Coatings on Metals." *Journal of Materials Science: Materials in Medicine.* vol. 10, pp. 401-409.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." *Chem. Commun.* pp. 1687-1688.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry.* vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling.* vol. 6, pp. 35-47.

Martinez, J. S., G. P. Zhang, P. D. Holt, H. -T. Jung, C. J. Carrano, M. G. Haygood, and Alison Butler. Feb. 18, 2000. "Self-Assembling Amphiphilic Siderophores from Marine Bacteria." *Science.* vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry.* vol. 275, No. 11, pp. 7701 -7707.

Cao, H., J. Y. Xu, E. W. Seelig, and R. P. H. Chang. May 22, 2000. "Microlaser Made of Disordered Media." *Applied Physics Letters.* vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery,* vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America.* vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly," *Nature.* vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coil* DsbC." *Journal of Biological Chemistry.* vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science.* vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell.* vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters.* vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America.* vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science.* vol. 9, pp. 1095-1105.

Archer, Eric A., Noah T. Goldberg, Vincent Lynch, and Michael J. Krische. 2000, "Nanostructured Polymer Duplexes via the Covalent Casting of 1-Dimensional H-Bonding Motifs: A New Strategy for the Self-Assembly of Macromolecular Precursors." *Journal of the American Chemical Society.* vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound. "*Langmuir.* vol. 16, No. 11, pp. 4929-4939.

Beniash, E., W. Traub, Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology.* vol. 132, pp. 212-225.

Bigi, Adriana, Elisa Boanini, Silvia Panzavolta, and Norberto Roveri. 2009. "Biomimetic Growth of Hydroxyapatite on Gelatin Films Doped with Sodium Polyacrylate." *Biomacromolecules.* vol. 1, No. 4, pp. 752-756.

Bourel, Line, Olivier Carion, Helene Gras-Masse, and Oleg Melnyk. 2000. "The Deprotection of Lys(Mtt) Revisited." *Journal of Peptide Science.* vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacronmolecules.* vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun.* pp. 367-368.

Chamberlain, L. J., I. V. Yannas, H-P. Hsu, G. R. Strichartz and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research.* vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research.* vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research.* vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers.* vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects.* vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta.* vol. 1475, pp. 346-352.

Langer, Robert. 2000. "Biomaterials in Drug Delivery and Tissue Engineering: One Laboratory's Experience." *Accounts of Chemical Research.* vol. 33. No. 2. pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med.* vol. 136, No.2 pp. 100-109.

Lu, Lichun, Susan J. Peter, Michelle D. Lyman, Hui-Lin Lai, Susan M. Leite, Janet A. Tamada, Shiro Uyama, joseph P. Vacanti, Robert Langer, and Antonios G. Mikos. 2000. "In Vitro and in Vivo Degradation of Porous Poly(dL-Lactic-co-Glycolic Acid) Foams." *Biomaterials.* vol. 21, pp. 1837-1845.

Matsuura, T., R. Hosokawa, K. Okamoto, T. Kimoto, and Y. Akagawa. 2000. "Diverse mechanisms of Osteoblast Spreading on Hydroxyapatite and Titanium." *Biomaterials.* vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research.* vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research.* vol. 61, pp. 302-312.

Sakiyama-Elbert, Shelly E. and Jeffrey A. Hubbell. 2000, "Controlled Release of Nerve Growth Factor from a Heparin-Containing Fibrin-Based Cell Ingrowth Matrix." *Journal of Controlled Release.* vol. 69, pp. 149-158.

Sakiyama-Elbert, Shelly E. and Jeffrey A. Hubbell. 2000, " Development of Fibrin Derivatives for Controlled Release of Heparin-Binding Growth Factors." *Journal of Controlled Release.* vol. 65, pp. 389-402.

Thareja, R. K. and A mitra. 2000. "Random Laser Action in ZnO." *Appl. Phys.* vol. B 71, pp. 181-184.

Tunggal, Patrick, Neil Smyth, Mats Paulsson, and Mark-Christoph Ott. 2000. "Laminins: Structure and Genetic Regulation," *Microscopy Research and Technique,* vol. 51, pp. 214-227.

do Serro, Ana Paula Valagao Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research.* vol. 49, pp. 345-352.

Yamada, norihiro and Katsuhiko Ariga. 2000. "Formation of β-Sheet Assemblage with a View to Developing an Amyloid Model." *Synlett.* vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science.* vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domins of Amphiphiles." *Journal of Colloid and Interface Science.* vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research.* vol. 59, pp. 312-320.

Jin, Young-Gu and K. J. Chang. Feb. 26, 2001. "Mechanism for the Enhanced Diffusion of Charged Oxygen Ions in $SiO_2$." *Physical Review Letters.* vol. 86, No. 9, pp. 1793-1796.

Orlic, Donald, Jan Kajstura, Stefano Chimenti, Igor Jakonuk, Stacie M. Anderson, Baocheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature.* vol. 410, pp. 701-705.

Vailhe, Bruno, Daniel Vittet, and Jean Jacques Feige. Apr. 2001. "In Vitro Models of Vasculogenesis and Angiogenesis." *Laboratory Investigation.* vol. 81, No. 4, p. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevsky, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science.* vol. 292, pp. 1897-1899.

Lee, Kuen Yong and David J. Mooney. Jul. 2001. "Hydrogels for Tissue Engineering." *Chemical Reviews.* vol. 101, No. 7, pp. 1869-1879.

Aggeli, A., I. A. Nyrkova, M. Bell, R. Harding, L. Carrick, T. C. B. McLeish, A. N. Semenov, and N. boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America.* vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Namofibers." *Science.* vol. 294, pp. 1684-1688.

Richardson, Thomas P., Martin C. Peters, Alessandra B. Ennett, and David J. Mooney. Nov. 2001. "Polymeric System for Dual Growth Factor delivery." *Nature Biotechnology.* vol. 19, pp. 1029-1034.

Matsui, Hiroshi and Robert MacCuspie. Dec. 2001. "Metalloporphyrin Nanotube Fabrication Using Peptide Nanotubes as Templates." *Nano Letters.* vol. 12, pp. 671-675.

Mathew, Mathai and Shozo Takagi. Nov.-Dec. 2001. "Structures of Biological Minerals in Dental Research." *Journal of Research of the National Institute of Standards and Technology.* vol. 106, No. 6, pp. 1035-1044.

Woo, Byung Ho, Betsy F. Fink, Richard Page, jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical research.* vol. 18, No. 12, pp. 1747-1753.

Barrere, F., P. Layrolle, C. A. Van Blitterswijk, and K. de Groot. 2001. "Biominmetic Goatings on Titanium: A Crystal Growth Study of Octacalcium Phosphate." *Journal of Materials Science: Materials in Medicine.* vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir.* vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science.* vol. 36, pp. 3253-3260.

Chang, John C., Gregory J. Brewer, and Bruce C. Wheeler. 2001. "Modulation of Neural Network Activity by Patterning." *Biosensors & Bioelectronics.* vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research.* vol. 55, pp. 503-511.

Doi, Tomokiyo, Takatoshi Kinoshita, Hiroki Kamiya, Shintaro Washizu, Yoshiharu Tsujita, and Hiroaki Yoshimizu. 2001. "Aggregation of Polypeptide-Based Amphiphiles in Water." *Polymer Journal.* vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir.* vol. 17, No, 17 pp. 5352-5360.

Hoess. Ronald H. 2001. "Protein Design and Phage Display." *Chemical Reviews.* vol. 101, No. 10, pp. 3205-3218.

Huang, Eric J. and Louis F. Reichardt. 2001. "Neurotrophins: Roles in Neuronal Development and Function." *Annual Review of Neuroscience.* vol. 24, pp. 677-736.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules.* vol. 2, No. 1, pp. 85-94.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials.* vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials.* vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research.* vol. 57, pp. 327-335.

Look, D. C. 2001. "Recent Advances in ZnO Materials and Devices." *Materials Science and Engineering.* vol. B80, pp. 383-387.

Luo, Yi and Glenn D. Prestwich. 2001. "Novel Biomaterials for Drug Delivery." *Expert Opin. Ther. Patents.* vol. 11, No. 9, pp. 1395-1410.

Marchi-Artzner, Valerie, Barbara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." *Chem. Eur. J.* vol. 7, No. 5, pp. 1095-1101.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules.* vol. 2, No. 1, pp. 85-94.

Matsui, Hiroshi. and Gary E. Douberly, Jr. 2001. "Organization of Peptide Nanotubes into Macroscopic Bundles. "*Langmuir.* vol. 17, No. 25, pp. 7918-7922.

Matsui, Hiroshi, Precila Porrata, and Gary E. Douberly, Jr. 2001. "Protein Tubule Immobilization on Self-Assembled Monolayers on Au Substrates." *Nano Letters.* vol. 1, No. 9, pp. 461-464.

Neet, K. E. and R. B. Campenot. 2001. "Receptor Binding, Internalization, and Retrograde Transport of Neurotrophic Factors." CMLS, Cell Mol. Life Sci. vol. 58, pp. 1021-1035.

Otsuka, Hidenori, Yukio Nagasaki, and Kazunori Kataoka. 2001. "Self-Assembly of Poly(ethylene glycol —based Block Copolymers for Biomedical Applications." *Current Opinion in Colloid & Interface* Science. vol. 6, pp. 3-10.

Shimizu Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the american Chemical Society.* vol. 123, No. 25, pp. 5947-5955, S1-S16.

Socrates, George. 2001. *Infrared and Raman Characteristic Group Frequencies: Tables and Charts.* Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir.* vol. 17, No. 3, pp. 866-872. Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research.* vol. 57, pp. 441-448.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research.* vol. 57, pp. 441-448.

Tanihara, Masao, Yasuo Suzuki, Eriko Yamamoto, Atsushi Noguchi, and Yutaka mizushima. 2001. "Sustained Release of Basic Fibroblast Growth Factor and Angiogenesis in a Novel Covalently Crosslinked Gel of Heparin and Alginate." *Journal of Biomedical Materials Research.* vol. 56, pp. 216-221.

Torchilin, Vladimir P. 2001. "Structure and Design of Polymeric Surfactant-Based Drug Delivery Systems." *Journal of Controlled Release.* vol. 73, pp. 137-172.

Yeung, C. K., L. Lauer, A. Offenhausser, and W. Knoll. 2001. "Modulation of the Growth and Guidance of Rat Brain Stem Neurons Using Patterned Extracellular Matrix Proteins." *Neuroscience Letters.* vol. 301, pp. 147-150.

Zubarev, Eugene R., Martin U. Pralle. Eli D. Sone, and Samuel I. Stupp. 2001. "Self-Assembly of Dendron Rodcoil Molecules into Nanoribbons." *Journal of the American Chemical Society.* vol. 123, No. 17, pp. 4105-4106 .

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry.* vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal.* vol. 16, pp. 213-215.

Zubarev, Eugene R., Martin U. Pralle, Eli D. Sone, and Samuel I. Stupp. Feb. 2002. "Scaffolding of Polymers Supramolecular Nanoribbons." *Advanced Materials.* vol. 14, No. 3, pp. 198-203.

Slocik, Joseph M., Joshua T. Moore, and David W. Wright. Mar. 2002. Monoclonal Antibody Recognition of Histidine-rich Peptide Encapsulated Nanoclusters. *Nano Letters.* vol. 2, No. 3, pp. 169-173.

Teng, Yang D., Erin B. Lavik, Xianln Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells" *Proceedings of the National Academy of Sciences of the United States of America.* vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature.* vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America.* vol. 99, No. 8, pp. 5355-5360.

Vauthey, Sylvain, Steve Santoso, Haiyan Gong, Nicki Watson, and Shuguang Zhang. Apr. 16, 2002. "Molecular Self-Assembly of surfactant-Like Peptides to Form Nanotubes and Nanovesicles." *Proceedings of the National Academy of Sciences of the United States of America,* vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide amphiphiles." *Nature.* vol. 417, pp. 424-428.

GrandPre, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Blight, Andrew R. Nov. 2002. "Miracles and Molecules—Progress in Spinal Cord Repair." Nature Neuroscience Supplement. vol. 5, pp. 1051-1054.

Chang, Hua, Chester W. Brown, and Martin M. Matzuk. Dec. 2002. "Genetic Analysis of the Mammalian Transforming Growth Factorβ Superfamily." vol. 23, No. 6, pp. 787-823.

Busque, Felix, Stephanie A. Hopkins, and Joseph P. Konopelski. "Progress Toward a Peptidomimetic of Laminin-Derived Pentapeptide YIGSR: Synthesis of the Unique Tricyclic Core Structure." *J. Org. Cyhem*. vol. 67, No. 17, pp. 6097-6103.

Canaple, Laurence, Annemie Rehor, and David Hunkeler. 2002. "Improving Cell Encapsulation Through Size Conirol." *J. Biomater. Sci. Polymer Edn*. vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Camparnelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariepy, Jean, Sandrine Remy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem*. vol. 13, No. 3, pp. 679-684.

Glaättli, Alice, Xavier Daura, Dieter Seebach, and Wilfred F. van Gunsteren. 2002. "Can One Derive The Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles," *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Coplymeric Micelles to $TiO_2$ Surfaces." *Langmuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Spinal Cord Injury in the Mouse: Part 2. Quantitative Neuroanatomical Assessment and Analysis of the Relationships Between Axonal Tracts, Residual Tissue, and Locomotor Recovery," *Journal of Neurotrauma*. vol. 19, No. 2, pp. 191-203.

Kruger, Ryan G., Patrick Dostal, and Dewey G. McCafferty. 2001. "An Economical and Preparative Orthogonal Solid Phase Synthesis of Fluorescein and Rbodamine Derivatized Peptides: FRET Substrates for the *Staphylococcus aureus* Sortase SrtA Transpeptidase Reaction." *Chem. Commun*. pp. 2092-2093.

Lauer, L., A. Vogt, C. K. Yeung, W. Knoll, and A. Offenhäer. 2002. "Electrophysiogical Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of β-Sheet Peptide." *Nano. Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." *Phys. Chem. Chem. Phys*. vol. 4, pp. 4051-4057.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science*. vol. 7, pp. 262-266.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." *Langmuir*. vol. 18, No. 8, pp. 3332-3335.

Thiebaud, Pierre, Lars Lauer, Wolfgang Knoll, and Andreas Offenhäuser. "PDMS Device for Patterned Application of Microfluids to Neuronal Cells Arranged by Microcontact Printing." *Biosensors & Bioelectronics*. vol. 17, pp. 87-93.

Tryoen-Toth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667

Wong, Michael S., Jennifer N. Cha, Kyoung-Shin Choi, Timothy Deming, and Galen D. Stucky. 2002. "Assembly of Nanoparticles into Hollow Spheres Using Block Copolypeptides." *Nano Letters.* vol. 2, No. 6, pp. 583-587.

Young, Wise. 2002. "Spinal Cord Contusion Models." *Progress in Brain Research.* vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Exuacellular Matrices," *Nature Biotechnology.* vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery.* vol. 14, No. 3, pp. 308-316.

Silva, G. A., K. L. Kehl, K. L. Niece, and S. I. Stupp. May 4, 2003. "Nanoengineered Peptide Amphiphile Network for Network for Photoreceptor Replacement in Degenerative Retinal Disorders." Investigative OPhthalmology & Visual Science. Abstract No. 492 from Annual Meeting of the Association for Research in Vision and Opthalmology.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery.* vol. 85-A, No. 8, pp. 1544-1552, 141.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical Sized Canine Segmental Defect." *The Journal of Bone & Joint Surgery.* vol. 85-A, No. 19, pp. 1927-1935.

Zhang, Shuguang. Oct. 2003. "Fabrication of Novel Biomaterials Through Molecular Self-Assembly." *Nature Biotechnology.* vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society.* vol. 125, No. 32, pp. 9619-9628.

Alsina, Jordi and Fernando Albericio. 2003. "Solid-Phase Synthesis of C-Terminal Modified Peptides." *Biopolymers (Peptide Science).* vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology.* vol. 14, pp. 559-565.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fementans." Eur. J. Biochem. vol. 270, pp. 3271-3279.

Czeisler, C., V. M. Tysseling-Mattiace, G. A. silva, S. I. Stupp, and J. A. Kessler. 2003. "Behavoral Improvement and Increased Survival Rate after Treatment with a Self Assembling Gel in a Rat Model of Spinal Cord Injury." 2003 Abstract Viewer/itinerary Planner. Program No. 245.22. Washington, DC: Society for Neuroscience. Printed Feb. 5, 2007. p. 1. http://sfn.scholarone.com/itin2003/main.html?new _page_idx1554 . . . .

Fauza, Dario O. 2003. "Tissue Engineering: Current State of Clinical Application." *Current Opinion in Pediatrics.* vol. 15, pp. 267-271.

Ganesh, S. and R. Jayakumar. 2003. "Structural Transition Involved in a Novel Amyloid-Like β-Sheet Assemblage of Tripeptide Derivatives." *Biopolymers.* vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers* vol. 70, pp. 346-354.

Gergely, C. S., P. Bar Yosef, R. Govrin-Lipman, F. Cuisinier, and H. Füredi-Milhofer. 2003. "The Deposition of Calcium Phosphates Within Polyelectrolyte Multilayer Films." *Key Engineering Materials.* vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules.* vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on *in Vivo* Vascularization." *Journal of Biomedical Materials Research.* vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules.* vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society.* vol. 125, No. 24, pp. 7146-7147.

Pavlov, Georges, Stephanie Finet, Karine Tatarenko, Evgueniya Korneeva, and Christine Ebel. 2003. "Conformation of Heparin Studied with Macromolecular Hydrodynamic Methods and X-ray Scattering." *Eur. Biophys. J.* vol. 32, pp. 437-449.

Schmidt, Christine E. and Jennie Baier Leach. 2003. "Neural Tissue Engineering: Strategies for Repair and Regeneration." Annu. Rev. Biomed. Eng. vol. 5, pp. 293-347.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology.* vol. 459, pp. 1-8.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance differentiation of Cocultured Neurosphere Cells and Promote Regeneration of Injured Spinal Cord." *Journal of Neuroscience Research.* vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-sheet Assembly." *Angew. Chem. Int. Ed.* vol. 42, pp. 5496-5499.

Zhang. Yan, Hongwei Gu, Zhimou Yang, and Bing Xu. 2003. "Supramolecular Hydrogels Respond to Ligand-Receptor Interaction." *Journal of the American Chemical Society.* vol. 125, No. 45, pp. 13680-13681.

Hirano, Yoshiaki and David J. Mooney. Jan. 5, 2004. "Peptide and Protein in Presenting Materials for Tissue Engineering." *Advanced Materials.* vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science.* vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience.* vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research.* vol. 94, pp. 664-670.

Anthony, Shawn G. Mar. 28-Apr. 1, 2004. "Self-Assembling Nanofiber Matrix for Bone Regeneration." *the 227$^{th}$ ACS National Meeting.* Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting.* Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America.* vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine.* vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience.* vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings.* vol. 36, pp. 2464-2465.

Matsumura, Sachiko, Shinobu Uemura, and Hisakazu Mihara. 2004. "Fabrication of Namofibers with Uniform Morphology by Self-Assembly of Designed Peptieds." *Chem. Eur. J.* vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research.* vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience.* vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets.* vol. 5, No. 1, pp. 1-15.

Sayle, Roger. Printed Nov. 9, 2005. "Physiological Ionization and pKa Prediction." http://ww.daylight.com/meetings/emug00/Sayle/pkapredict.html. pp. 1-13.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." *Acta Biomaterialia.* vol. 1, pp. 387-397.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters.* vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters.* vol. 5, No. 2, pp. 249-252.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." *Langmuir.* vol. 21, No. 3, pp. 1001-1008.

Loudon, M. "Amino Acid Structures at Physiological pH." Printed Jun. 5, 2006. www.brynmawr.edu/Acads/Chem/mnerzsto/amino_acids_2.gif, and amino_acids3.htm.

Hoke, Ahmet. Aug. 2006. "Mechanisms of disease: What Factors Limit the Success of Peripheral Nerve Regeneration in Humans?" *Nature Clinical Practice Neurolog.* vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetie and Bioactive Peptide-Amphiphiles." *Soft Matter.* vol. 2, pp. 1015-1024.

"AccessScience Search Results. Amphiphile." Accessed online May 7, 2007. http://www.accessscience.com/search/asearch?locationxtitlestext&newsSearchx1&pubprivxprivate &categoriesxdictionalry&categvalxdictionary&textxamphiphile. McGraw-Hill Encyclopedia of Science & Technology Online.

The LabRat.com. 2007, updated. Hank's Buffered Salt Solution (HBSS) Recipe. http://www.thelabrat.com/protocolsHanks.shtml. Printed Jan. 19, 2007. pp. 1-2.

Tam, James P. 1996. "Recent Advances in Multiple Antigen Peptides." Journal of Immunological Methods. vol. 196, pp. 17-32.

Merkler, Doron. Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." The Journal of Neuroscience. vol. 21, No. 10, pp. 3665-3673.

Bonnet, Dominique, Kader Thiam, Estelle Loing, Oleg Minyk, and Hélène Gras-Masse. 2001. Synthesis by Chemoselective Ligation and Biological Evaluation of Novel Cell-Permeable PKC-7, Pseudosubstrate Lipopeptides. J. Med. Chem. vol. 44, No. 3, pp. 468-471.

Grothe, Claudia and Guido Nikkhah. 2001. "The role of Basic Fibroblast Growth Factor in Peripheral Nerve Regeneration." Anat. Embryol. vol. 204, pp. 171-177.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That Is Induced to Self- Assemble Under Physiological Conditions." Biosis. Society for Neuroscience Abstract Viewer and Itinerary Planner—2002. Abstract No. 825.4. 32nd Annual Meeting of the Society for Neuroscience; Orlando, Florida.

Leng, J., S. U. Egelhaaf, and M. E. Cates. Sep. 2003. "Kinetics of the Micelle-to-Vesicle Transition: Aqueous Lecithin-Bile Salt Mixtures." Biophysical Journal. vol. 85, No. 3, pp. 1624-1646.

Copping, Aaron M. and Vanda R. G. Pond. Dec. 9, 1950. "Folic Acid as a Growth-Factor for the Rat." Nature. No. 4232, p. 993.

Mulloy, Barbara and Mark J. Forster. 2000. "Conformation and Dynamics of Heparin and Heparan Sulfate." Glycoliology. vol. 10, No. 11, pp. 1147-1156.

Bruggeman, Holger, Sebastian Baumer, Wolfgang Florian Fricke, Amim Wiezer, Heiko Liesegang, Iwona Decker, Christina Herzberg. Rosa martinez-Arias, Rainer Meri, Anke Henne, and Gerhard Gottschalk. Feb. 4, 2003. "The Genome Sequence of *Clostridium tetani*, the Causative Agent of Tetanus Disease." PNAS. vol. 100, No. 3, pp. 1316-1321.

Invitrogen. Printed Jan. 22, 2008. "Dulbecco's Modified Eagle medium (D-MEM) (1X) Liquid (High Glucose)." http://www.invitrogen.com/content.cfm?pageld=95&fuseaction=MediaForm.dsp_mediaForm&productld . . . .

Uniprot entry for Q899Z6. Printed Mar. 14, 2008. http://www.pir.uniprot.org//cgi-bin/upEntry?id=Q899Z6_CLOTE. 3 pages.

Kibbey, Maura C., Mathias Juoker, Benjamin S. Weeks, Rachael L. Neve, William E. Van Nostrand, and Hynda K. Kleinman. Nov. 1993 "β-Amyloid Precursor Protein Binds to the Neurite-Promoting IKVAV Site of Laminin." Proc. Natl. Acad. Sci. U.S.A. vol. 90, pp. 10150-10153.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." Neurosurgery Online. vol. 38, No. 4, pp. 733-736.

Rapaport, Hanna, Kristian Kjaer, Torben R. Jensen, Leslie Leiserowitz, and David A. Tirrell. 2000. "Two-Dimensional Order in β-Sheet Peptide Monolayers." Journal of the American Chemical Society. vol. 122, No. 50, pp. 12523-12529.

Avrahami, Dorit and Yechiel Shai. 2002. "Conjugation of a Magainin Analogue with Lipophilic Acids Controls Hydrophobicity, Solution Assembly, and Cell Selectivity." Biochemistry. vol. 41, No. 7, pp. 2254-2263.

Yamada, Masanori, Yuiohi Kadoya, Shingo Kasai, Kozue Kato, Mayumi Mochizuki, Norio Nish, Nobutiisa Watanabe, Hynda K. Kleinman, Yoshihiko Yamada, and Motoyoshi Nomizu. 2002. "lle-Lys-Val-Ala-Val (IKVAV)-Containing Laminin α1 Chain Peptides Form Amyloid-like Fibrils." FEBS Letters. vol. 530, pp. 48-52.

McGregor, Clare-Louise, Lu Chen, Neil C. Pomroy, Peter Hwang, Sandy Go, Avijit Chakrabartty, and Gilbert G. Prive. Feb. 2003. "Lipopeptide Detergents Designed for the Structural Study of Membrane Proteins." Nature Biotechnology. vol. 21, pp. 171-176.

Ohmori, Hideya, Yasumitsu Sato, and Akiyoshi Namiki. 2004. "The Anticonvulsant Action of Propofol on Epileptiform Activity in Rat Hippocampai Slices." Anesth. Analg. vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." European Journal of Neuroscience. vol. 20, pp. 719-728.

Sone, Eli D. and Samuel I. Stupp. 2004. "Semiconductor-Encapsulated Peptide-Amphiphile Nanofibers." Journal of the American Chemical Society. vol. 126, No. 40, pp. 12756-12757.

Smith, L. A. and P. X. Ma. 2004. "Nano-•Fitxotrs Scaffolds for Tissue Engineering." Colloids and Surfaces. B: Blointerfaces. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures," J. Phys. Chem. B. vol. 108, No. 26, pp. 8817-8822.

Tsonchev, Stefan, Alessandro Troisi, George C. Schatz, and Mark A. Rather. 2004. "All-Atom Numerical Studies of Self-Assembiy of Zwitterionic Peptide Amphiphiles," J. Phys. Chem. B. vol. 108, No. 39, pp. 15278-15284.

Tsonchev, Stefan, Alessandro Troisi, George C. Schatz, and Mark A. Ratner. 2004. "On the Structure and Stability of Self-Assembied Zwitterionic Peptide Amphiphiles: A Theoretical Study." Nano Letters. vol. 4, No. 3, pp. 427-431.

Arnold, Michael S., Mustafa O. Guler, Mark. C. Hersam, and Samuel I. Stupp. 2005 "Encapsulation of Carbon Nanotubes by Self-Assembling Peptide Amphiphiles." Langmuir. vol. 21, No. 10, pp. 4705-4709.

Behanna, Heather A. Jack J. J. M. Donners, Alex C. Gordon, and Samuel I. Stupp. 2005. "Coassembly of Amphiphiles with Opposite Peptide Polarities into Nanofibers." Journal of the American Chemical Society. vol. 127, No. 4, pp. 1193-1200.

Bilton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." Langmuir. vol. 21, No. 25, pp. 11888-11895.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." Bioconjugate Chem. vol. 16, No. 6, pp. 1343-1348.

de Loos, Maaike, Ben L. Feringa, and Jan H. van Esch. 2005. "Design and Application of Self-Assembled Low Molecular Weight Hydrogels." Eur. J. Org. Chem. pp. 3615-3631.

Guler, Mustafa O., Randal C. Claussen, and Samuel I. Stupp. 2005. "Encapsulation of Pyrene Within Self-Assembled Peptide Amphiphile Nanofibers." Journal of Materials Chemistry. vol. 15, pp. 4507-4512.

Guler, Mustafa O., Jonathan K. Pokorski, Daniel H. Amelia, and Samuel I. Supp. 2005. "Enhanced Oligonucleotide Binding to Self-Assembled Nanofibers." Bioconjugate Chem. vol. 16, No. 3, pp. 501-503.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Adv. Mater. vol. 17, pp. 2612-2617.

Silva, Gabriel A. 2005. "Nanotechnology Approaches for the Regeneration and Neuroprotection of the Central Nervous System," Surwcal Neurology, vol. 63, pp. 301-306.

Silva, Gabriel A. 2005. "Small Neuroscience: The Nanostructure of the Central Nervous System and Emerging Nanotechnology Appiications." Current Nanoscience. vol. 1, No. 3, pp. 225-236.

Solis., F. J., S. I. Stupp, and M. Olvera de to Cruz, 2005. "Charge Induced Pattern Formation on Surfaces: Segregation in Cylindrical Micelles of Cationic-Anionic Peptide-Amphiphiles." The Journal of Chemical Physics. vol. 122, No. 5, 054905-1-054905-9.

Tovar, John D. Randal C. Claussen, and Samuel I. Stupp. 2005, "Probing the Interior of Peptide Amphiphile Supramolecular Aggregates" Journal of the American Chemical Society. vol. 127, No. 20, pp. 7337-7345.

Hosseinkliani, Hossein, Mohsen Hossernkhani, and Hisatoshi Kobayashi, Jul. 2006, "Design of Tissue-Engineered Nanoscaffold Through Self-Assembly of Peptide Amphiphile." Journal of Bioactive and Compatble Polymers. vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification," Cell. Vol. 126, pp, 677-689. Bn.insveld, L., J. Kuhlmann, and H. Waldmann. 2006. "Synthesis of Palmitoylated Ras-Peptides and --Proteins." Methods. Vol. 40, pp. 151-165.

Brunsveld, L., Kuhlmann, and H. Waldmann. 2006. "Synthesis of Palmitoylated Ras-Peptides and —Proteins." Methods. vol. 40, pp. 151-165.

Elgersma, Ronald C., Tania Meijneke, Remco de Jong, Arwin J. Brouwer, George Postburna, Dirk T. S. Rijkers, and M. Rob M. J. Liskamp. 2006. "Synthesis and Structural Investigations of N-alkylated β-peptidosdifonamide- peptide Hybrids of the Amyloidogenic Annylin(20-29) Sequence: Implications of Supramolecular Folding for the Design of Peptide-Based Bionanomaterials." Organic & Biomolecular Chemistry. vol. 4, pp. 3587-3597.

Guler, Mustafa 0., Lorraine Hsu; Stephen Soukasene, Daniel A. Harrington, James F. Hulvat, and Samuel I. Stupp. 2006. "Presentation of RGDS Epitopes on Self-Assembled Nanofibers of Branched Peptide Arnphiphiles." Biomacromolecules. vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." Journal of Biomedical Materials Research Part A. pp. 157-167.

Hosseinkhani, Hossein, Mohsen Hosseinkhani, Ali Khadembosseini, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration" Biomaterials. vol. 27, pp. 5836-5844.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." Langmuir. vol. 22, No. 7, pp. 3259-3264.

Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." Journal of the American Chemical Society. vol. 128, No. 22, pp. 7291-7298.

Rajangam, Kanya, Heather A. Behanna, Michael J. Hui, Xiaogiang Han, James F. Hulvat, Jon W. Lomasney, and Samuel I. Stupp. 2006. "Heparin Binding Nanostructures to Promote Growth of Blood Vessels." Nano Letters. vol. 6, No. 9, pp. 2086-2090.

Reches, Meital and Ehud Gazit. 2006. "Molecular Self-Assembly of Peptide Nanostructures: Mechanism of Association and Potential Uses." Current Nanoscience. vol. 2, No. 2, pp. 105-111.

Stendahi, John C., Mukti S. Rao, Mustafa 0. Guler. And Samuel I. Stupp. 2006. "Intermolecular Forces in the Self-Assembly of Peptide Amphiphile Nanofibers." Advanced Functional Materials. vol. 16, pp. 499-508.

Behanna, Heather A., Kanya Rajangam, and Samuel I. Stupp. 2007. "Modulation of Fluorescence Through Coassembly of Molecules in Organic Nanostructures." Journal of the American Chemical Society. vol. 129, No. 2, pp. 321-327.

Meijer, Joris T., Marjolijn Roeters, Valentina Viola, Dennis W. P. M. Lowik, Gert Vriend, and Jan C. M. van Hest. 2007. "Stabilization of Peptide Fibrils by Hydrophobic Interaction." Langmuir. vol. 23, No. 4, pp. 2058-2063.

Clemetson, K. J., and J. M. Clemetson. 1998. "Integrins and Cardiovascular Disease," CMLS Cellular and Molecular Life Sciences, vol. 54, pp. 502-513.

Dupin, Elisabeth, and Nicole M. Le Douarin. 2003. "Development of Melanocyte Precursors from the Vertebrate Neural Crest" Oncogene. vol. 22, pp. 3016-3023.

Mardilovich, Anastasia, and Efrosini Kokkoli. 2004. "Bibmirnetc Peptide—Amphiphiies for Functional Biomaterials: The Role of GRGDSP and PHSRN." Biomacromolecules. vol. 5, No. 3, pp. 950-957.

Niece, Krista L., Catherine Czeisler, Vibhu Sahni, Vicki Tysseling-Mattiace, Eugene T. Pashuck, John A. Kessler, and Samuel I. Stupp. 2008. "Modification of Gelation Kinetics in Bioactive Peptide Amphiphiies." Biomatertals. vol. 29, pp. 4501-4509.

Hui, Michael. May 24, 2004. "Heparin Binding Peptide Amphiphile and Transforming Growth Factor: A Novel Approach to Anti-Angiogenic Drug Delivery." The Second Annual Undergraduate Research Symposium. Retrieved //www.northwestern.edu/provost/students/research_symposium/program2004.pdf on Oct. 14, 2009. 45 pages.

Wayback Machine. www.archive.org/web/ entry. 1 page for www.northwestern.edu/provost/students/research_symposiumiprogram2004.pdf retrieved on Oct. 14, 2009.

* cited by examiner

C₁₆H₃₁O-NH-AAAAGGGEIKVAV-COOH    PA 25

C₁₆H₃₁O-NH-AAAAGGGKYIGSR-CONH₂    PA 24

C₁₆H₃₁O-NH-CCCCGGGS(P)RGDS-COOH    PA 23

SEQUENCE LISTING

```
<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Lys Val Ala Val
  1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 2

Cys Cys Cys Cys Gly Gly Gly Ser Arg Gly Asp
  1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 3

Cys Cys Cys Cys Gly Gly Gly Ser
```

```
       1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 4

Cys Cys Cys Cys Gly Gly Gly Ser Arg Gly Asp
  1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 5

Cys Cys Cys Cys Gly Gly Gly Ser Arg Gly Asp
  1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 6

Cys Cys Cys Cys Gly Gly Gly Ser Arg Gly Asp
  1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ser(P)

<400> SEQUENCE: 7

Gly Gly Gly Ser Arg Gly Asp
  1               5

<210> SEQ ID NO 8
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ser(P)

<400> SEQUENCE: 8

Gly Gly Gly Ser Arg Gly Asp
 1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 9

Ala Ala Ala Ala Gly Gly Gly Ser Arg Gly Asp
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 10

Ala Ala Ala Ala Gly Gly Gly Ser Arg Gly Asp
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 11

Cys Cys Cys Cys Gly Gly Gly Ser Lys Gly Glu
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)
```

```
<400> SEQUENCE: 12

Ala Ala Ala Ala Gly Gly Gly Ser Lys Gly Glu
 1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 13

Ala Ala Ala Ala Gly Gly Gly Ser Lys Gly Glu
 1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 14

Cys Cys Cys Cys Gly Gly Gly Ser Arg Gly Asp
 1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Cys Cys Cys Gly Gly Gly Ser Arg Gly Asp
 1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Cys Cys Cys Gly Gly Gly Glu Ile Lys Val Ala Val
 1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)
<223> OTHER INFORMATION: Ser(P)

<400> SEQUENCE: 17

Cys Cys Cys Cys Gly Gly Gly Ser Arg Gly Asp Ser
 1               5                  10

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid

<400> SEQUENCE: 18

Leu Leu Leu Lys Lys Xaa
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: variable amino acid

<400> SEQUENCE: 19

Leu Ser Leu Ser Xaa
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Ile Gly Ser Arg
 1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Cys Cys Cys Gly Gly Gly Lys Ile Lys Val Ala Val
 1               5                  10

<210> SEQ ID NO 22
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 22

Ala Ala Ala Ala Gly Gly Gly Lys Tyr Ile Gly Ser Arg
  1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ala Ala Gly Gly Gly Glu Ile Lys Val Ala Val
  1               5                  10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Ala Gly Gly Glu Gln Ser
  1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ala Ala Gly Gly Gly Glu Arg Gly Asp Ser
  1               5                  10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Cys Cys Cys Gly Gly Gly Ser
  1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Cys Cys Cys Gly Gly Gly Glu
  1               5
```

-continued

```
<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 28

Ala Ala Ala Ala Gly Gly Gly Ser
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ala Ala Gly Gly Gly Ser
 1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ser(P)

<400> SEQUENCE: 30

Gly Gly Gly Ser
 1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Ser
 1
```

SELF-ASSEMBLY OF PEPTIDE-AMPHIPHILE NANOFIBERS UNDER PHYSIOLOGICAL CONDITIONS

This application is a divisional of U.S. patent application Ser. No. 10/368,517, filed Feb. 18, 2003, now U.S. Pat. No. 7,371,719, which claims priority from U.S. provisional application Ser. No. 60/357,228 filed Feb. 15, 2002, both of which are incorporated herein in their entireties by reference.

This invention was made with government support under Grant Number DMR-9996253 awarded by the National Science Foundation, and Grant Number F49620-00-1-0283/P01 awarded by the Air Force Office of Scientific Research (MURI), and Grant Number DE-FG02-00ER45810 awarded by the Department of Energy. The government has certain rights in the invention.

BACKGROUND OF THE INVENTION

Self-assembly and biomineralization are used for fabrication of many composite materials. Natural bone tissue is a particularly complex example of such a composite with multiple levels of hierarchical organization (S. Weiner, H. D. Wagner, *Annu. Rev. Mater. Sci.* 28, 271-298 (1998)). At the lowest level of this hierarchy is the organization of collagen fibrils with respect to hydroxyapatite (HA) crystals. Collagen fibrils are formed by self-assembly of collagen triple helices while the HA crystals grow within these fibrils in such a way that their c-axes are oriented along the long axes of the fibrils (W. Traub, S. Weiner, *Proc. Nat. Acad. Sci.* 86, 9822-9826 (1989)). The preparation of any material with structure on the nanoscale is a challenging problem. Fabrication of materials that resemble bone, even at the lowest level of hierarchical organization, is even more difficult because it involves two dissimilar organic and inorganic nanophases that have a specific spatial relationship with respect to one another. One approach, using an artificial system, has been to prepare an organic nanophase designed to exert control over crystal nucleation and growth of the inorganic component.

The controlled nucleation and growth of crystals from organic templates has been demonstrated in in vitro experiments and in a number of natural biomineralizing systems (S. Mann, J. P. Hannington, R. J. P. Williams, *Nature* 324, 565-567 (1986); D. D. Archibald, S. Mann, *Nature* 364, 430-433 (1993); S. L. Burkett, S. Mann, *Chem. Commun.* 321-322 (1996); S. I. Stupp, P. V. Braun, *Science* 277, 1242-1248 (1997); J. Aizenberg, A. J. Black, G. M. Whitesides, *Nature* 398, 495-498 (1999); S. R. Whaley, D. S. English, E. L. Hu, P. F. Barbara, A. M. Belcher, *Nature* 405, 665-668. (2000); L. Addadi, S. Weiner, *Angew. Chem., Int. Ed. Engl.* 31, 153-169 (1992); S. Mann, *J. Chem. Soc., Dalton Tran.* 3953-3961 (1997); S. Weiner, L. Addadi, *J. Mater. Chem.* 7, 689-702 (1997)). These studies on templated crystal growth suggest that nucleation occurs on surfaces exposing repetitive patterns of anionic groups. Anionic groups tend to concentrate the inorganic cations creating local supersaturation followed by oriented nucleation of the crystal. Many groups have investigated the preparation of bone-like materials using three dimensional organic substrates such as poly(lactic acid), reconstituted collagen and many others, and some studies shows a similar correlation between the crystallographic orientation of hydroxyapatite when the organic scaffold is made from reconstituted collagen (G. K. Hunter, H. A. Goldberg, *Biochem. J.* 302, 175-179 (1994); G. M. Bond, R. H. Richman, W. P. McNaughton, *J. Mater. Eng. Perform.* 4, 334-345 (1995); J. H. Bradt, M. Mertig, A. Teresiak, W. Pompe, *Chem. Mater.* 11, 2694-2701 (1999); N. Ignjatovic, S. Tomic, M. Dakic, M. Miljkovic, M. Plavsic, D. Uskokovic, *Biomaterials* 20, 809-816 (1999); F. Miyaji, H. M. Kim, S. Handa, T. Kokubo, T. Nakamura, *Biomaterials* 20, 913-919 (1999); H. K. Varma, Y. Yokogawa, F. F. Espinosa, Y. Kawamoto, K. Nishizawa, F. Nagata, T. Kameyama, *J. Mater. Sci.: Mater. Med.* 10, 395-400 (1999); A. Bigi, E. Boanini, S. Panzavolta, N. Roveri, *Biomacromolecules* 1, 752-756 (2001); M. Kikuchi, S. Itoh, S. Ichinose, K. Shinomiya, J. Tanaka, *Biomaterials* 22, 1705-1711 (2001)). However, such results have never been demonstrated in a pre-designed and engineered self-assembling molecular system.

BRIEF DESCRIPTION OF THE DRAWINGS

FIG. 7, Top: Molecule #4 containing a C10 alkyl tail. Bottom: Molecule #13 containing a C22 alkyl tail; FIG. 8, Top: Molecule 8 utilizing a tetra alanine sequence in place of tetra cysteine and containing a C16 alkyl tail. Bottom: Molecule 9 utilizing a tetra alanine sequence in place of tetra cysteine and containing a C10 alkyl tail; and FIG. 9, peptide-amphiphiles with three different peptide head groups. Top: Molecule 10 with "KGE". Middle: Molecule 14 lacking the phosphoserine group. Bottom: Molecule 15 with (SEQ ID NO: 1) "IKVAV."

FIGS. 10a-10b. Chemical structures of PA compositions 21 and 22, with reference to Table 2, below.

SUMMARY OF THE INVENTION

Figure 1A:
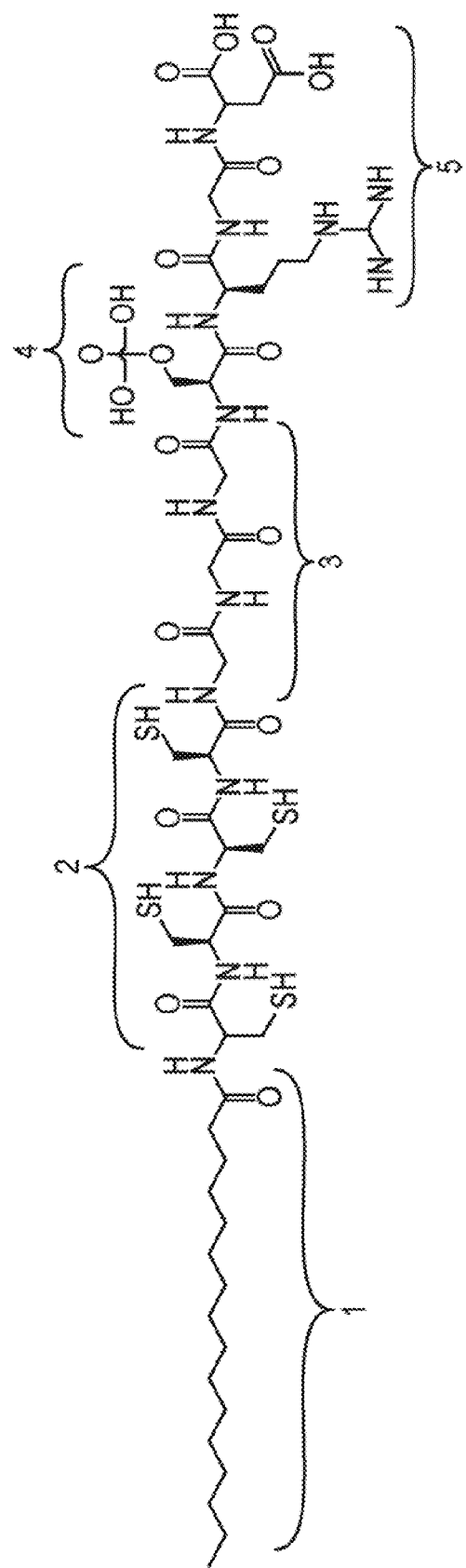
FIG. 1. In accordance with this invention: a) Chemical structure of a preferred peptide amphiphile, highlighting one or more structural features thereof. Region 1 may comprise a long alkyl tail that conveys hydrophobic character to the molecule and combined with the peptide region makes the molecule amphiphilic. Region 2 may comprise one or more (four consecutive, shown) cysteine residues which when oxidized may form disulfide bonds to provide a desired robust self-assembled structure. Region 3 may comprise a flexible linker region of one or more glycine residues, preferably three, or functionally similar such residues or monomers, to provide the hydrophilic head group flexibility from the more rigid crosslinked region. Region 4 may comprise a single phosphorylated serine residue which is designed to interact strongly with calcium ions and help direct mineralization of hydroxyapatite. Region 5 may comprise cell adhesion ligand Arg-Gly-Asp (RGD). b) Molecular model of an illustrated PA showing the overall conical shape of the molecule going from the narrow hydrophobic tail to the bulkier peptide region. c) Schematic showing the self-assembly of PA molecules into a cylindrical micelle.

In light of the foregoing, it is an object of the present invention to provide a nanostructured fiber-like system, or nanostructure providing other shapes such as spherical or oblate, and/or molecular components thereof, together with various methods for assembly and use to recreate or mimic the structural and/or functional interaction between collagen fibrils and hydroxyapatite crystals in bone or an extracellular matrix, thereby providing a nanostructured approach divergent from the prior art. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a composition which can be used for assembly of a molecular structure having dimensional and functional characteristics biomimetic with collagen fibrils.

It can also be an object of the present invention to provide a nanostructured fibrous system as a template for tissue development.

It can also be an object of the present invention to provide a composite of a mineralized nanofiber structure biomimetic with collagen fibrils and hydroxyapatite crystals in natural bone tissue.

It can also be an object of the present invention to provide a system for the facile self-assembly of nanostructured fibers under a particular pH regime or under substantially neutral or physiological pH conditions, for use in conjunction with one or more of the preceding objectives, such fibers as can be reversibly stabilized to promote structural integrity.

It can also be an object of the present invention to provide peptide amphiphile compositions comprising two or more oppositely charged peptide components, each such component as can further include the same or a differing bioactive epitope sequence, for subsequent biomedical applications including without limitation either in vitro or in vivo drug delivery, cell therapies or tissue engineering.

It can also be an object of the present invention, irrespective of any end use application, to provide one or more peptide amphiphile compositions which are stable at physiological pHs with or without covalent cross-linking, such stability of as can be provided via ionic cross-linking of charged functional groups present within the component amphiphiles of such compositions.

It can also be an object of the present invention to provide a methodology using fibers in a stabilized three-dimensional structure to direct and/or control mineralization and crystal growth thereon.

It can also be an object of the present invention to provide a molecular system for the design and engineering of specific nanofibers and components thereof to target particular cell and/or mineral growth en route to a variety of hard or soft biomimetic materials for biological and non-biological applications, the later including, but not limited to, catalysis, photonics and electronics.

Other objects, features, benefits and advantages of the present invention will be apparent from this summary and its descriptions of various preferred embodiments, and will be readily apparent to those skilled in the art having knowledge of natural biomineralizing systems. Such objects, features, benefits and advantages will be apparent from the above as taken into conjunction with the accompanying examples, data, figures and all reasonable inferences to be drawn therefrom.

With respect to various embodiments, the present invention comprises use of self-assembly techniques, such self-assembly as may be employed in conjunction with mineralization to prepare a nanostructured composite material which recreates or mimics the structural orientation and interaction between collagen and hydroxyapatite observed in bone. A composite may be prepared by self-assembly, covalent capture, and mineralization of one or more peptide-amphiphile (PA) compositions. As evident from the preceding, the peptide-amphiphile (PA) compositions of this invention can be synthesized using preparatory techniques well-known to those skilled in the art—preferably, by standard solid phase chemistry, with alkylation or other modification of the N-terminus of the peptide component with a hydrophobic moiety. Mono or di-alkyl moieties attached to the N or C termini of peptides may influence their aggregation and secondary structure in water in both synthetic and natural systems. As illustrated in several embodiments, a hydrophobic, hydrocarbon and/or alkyl tail component with a sufficient number of carbon atoms coupled to an ionic peptide having a preference for beta-strand conformations can in certain embodiments be used to create an amphiphile that assembles in water into nanofiber structures. The amphiphile's overall conical shape can also have an effect on such assemblies. (J. N. Israclachvili *Intermolecular and surface forces;* 2nd ed.; Academic: London San Diego, 1992). The hydrophobic tails pack in the center of the assembly with the peptide segments exposed to an aqueous or hydrophilic environment. These cylindrical nanostructures can be viewed as fibers in which the chemistry of the peptide region is repetitively displayed on their surface. Comparably, consistent with this invention, amphiphile molecules can also be designed to provide micelles having structural shapes that may differ from a fiber like appearance.

Without limitation, three structural and/or functional features can be engineered into the peptide region of a PA composition of this invention. First, the prepared fibers are optimally robust and, for this reason, one or more cysteine amino acid residues—four in some embodiments and/or, optionally, consecutive—can be incorporated in the sequence for covalent capture of supramolecular nanofibers. (D. Y. Jackson, D. S. King, J. Chmielewski, S. Singh, P. G. Schultz, *J. Am. Chem. Soc.* 113, 9391-9392 (1991); T. D. Clark, K. Kobayashi, M. R. Ghadiri, *Chem Eur J* 5, 782-792 (1999); Y. Y. Won, H. T. Davis, F. S. Bates, *Science* 283, 960-963 (1999); E. R. Zubarev, M. U. Pralle, L. M. Li, S. I. Stupp, *Science* 283, 523-526 (1999); E. A. Archer, N. T. Goldberg, V. Lynch, *J Am Chem Soc* 122, 5006-5007 (2000); F. Cardullo, M. C. Calama, B. H. M. Snellink-Ruel, J. L. Weidmann, A. Bielejewska, R. Fokkens, N. M. M. Nibbering, P. Timmerman, D. N. Reinhoudt, *Chem. Comm.* 5, 367-368 (2000)). Such residues can be used to form disulfide bonds between adjacent PA molecules upon oxidation to lock the supramolecular structure into place. The formation of the disulfide bonds is reversible, as described elsewhere herein, allowing self correction of improper disulfide bonds or return to the supramolecular structure by treatment with mild reducing agents.

With regard to a second feature, the fibers of various embodiments may be able to nucleate the formation of HA crystals in the proper environment. It is well known that acidic moieties play a key role in biomineralization processes and in the formation of calcium phosphate minerals phosphorylated groups are particularly important. (G. K. Hunter, H. A. Goldberg, *Biochem. J.* 302, 175-179 (1994); S. Weiner, L. Addadi, *J. Mater. Chem.* 7, 689-702 (1997)). For example in dentin, the phosphophoryn protein family contains numerous repeats of the sequences Asp-Ser(P)-Ser(P) and Ser(P)-Asp (A. George, L. Bannon, B. Sabsay, J. W. Dillon, J. Malone, A. Veis, N. A. Jenkins, D. J. Gilbert, N. G. Copeland, *J. Biol. Chem.* 271, 32869-32873 (1996)). These massively phosphorylated proteins are closely associated with the collagen extracellular matrix (ECM) and are known to play an important role in HA mineralization (A. Veis In *Biomineralization: Chemical and Biological Perspectives*; S. Mann, J. Webb, J. R. P. Williams, Eds.; VCH: Weinheim N.Y., 1989; pp 189-222). Accordingly, at least one phosphoserine residue can be incorporated into the peptide sequence which, after self assembly, allows the fiber to display a highly phosphorylated surface functionally biomimetic to a long peptide segment. This, in part, may be used to simulate a repetitive organization of phosphate groups found in phosphophoryn proteins.

Figure 1:
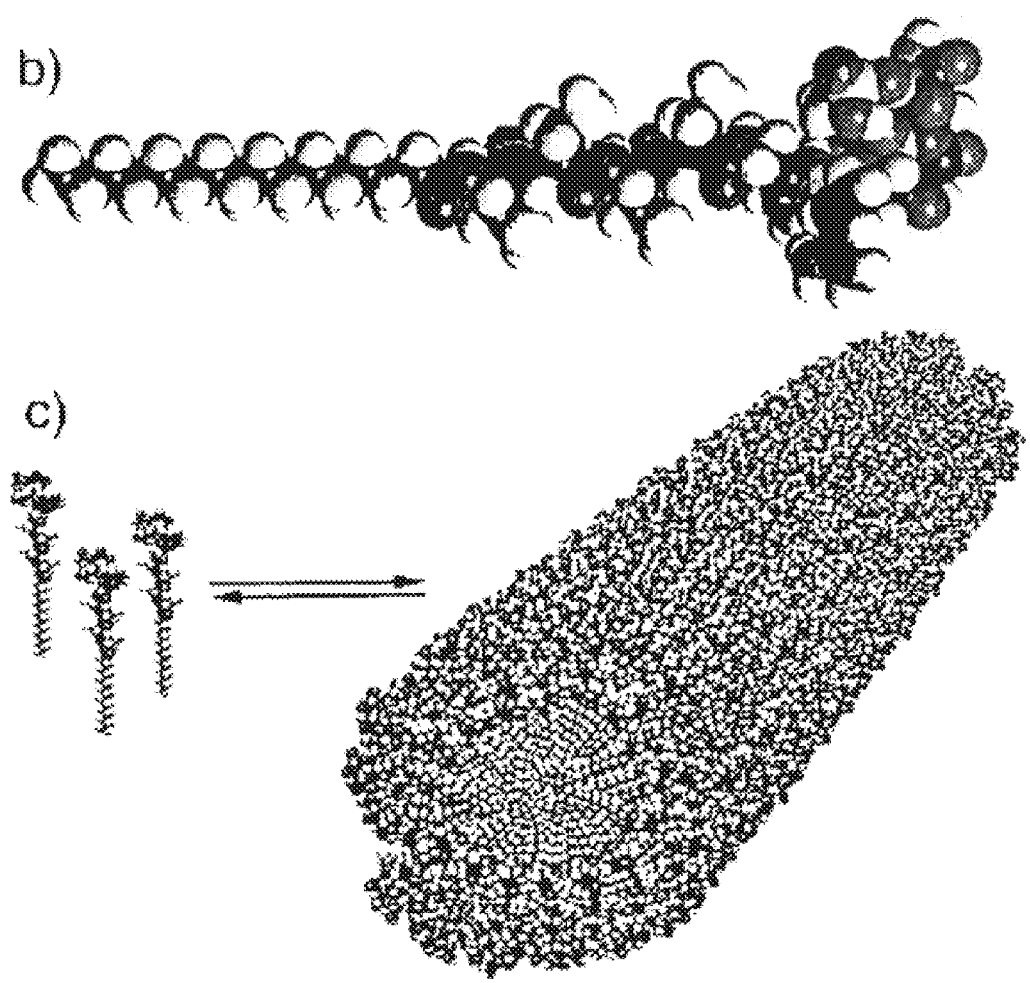

Third, with respect to one or more of the preceding embodiments or others within the scope of this invention, it would be beneficial for biomedical applications to provide fibers promoting surface adhesion and growth of cells. Another collagen associated protein, fibronectin, contains the sequence Arg-Gly-Asp (RGD). As this sequence has been found to play an important role in integrin-mediated cell adhesion, an RGD sequence can also be included in preferred peptide components and/or PA compositions, depending upon end-use application. Collectively, these and other design principles led to preparation of a PA molecule of the type shown in FIG. 1. While the PA compound of FIG. 1 is shown with a bioactive RGD sequence, other epitope sequences can be used, as described elsewhere herein including, but not limited to, the IKVAV (SEQ ID NO: 1) sequence.

Notwithstanding the numerous embodiments provided above, broader aspects of the present invention include a peptide amphiphile compound/composition having 1) a hydrophobic component and 2) a peptide or peptide-like component further including a bioactive epitope sequence. In various preferred embodiments, the hydrophobic component of such a compound or composition is of sufficient length to provide amphiphilic behavior and nanofiber assembly/formation in water or another polar solvent system. Typically, such a component may be about a $C_6$ or greater hydrocarbon moiety, although other hydrophobic, hydrocarbon and/or alkyl components could be used as would be well-known to those skilled in the art to provide similar structural or functional effect. Such hydrophobic components include, without limitation, cholesterol, biphenyl and p-aminobenzoic acid. Regardless, a peptide component of such a composition may include the aforementioned RGD sequence found especially useful for the nanofiber cell adhesion and mineralization described herein. Alternatively, an IKVAV (SEQ ID NO: 1) sequence can be incorporated into a PA compound.

Preferred peptide components of such compounds/compositions can also include a phosphoryl-functionalized residue or sequence (as indicated with the corresponding letter code and a parenthetical "P"), as described above. Inclusion of a phosphoserine residue, S(P), has been found especially useful for HA mineralization. Other embodiments can include, for example and without limitation, a phosphotyrosine residue. The peptide component of such compositions can also include a residue or sequence capable of promoting intermolecular bonding and structural stability of the micelles/nanofibers available from such compositions. A sequence of cysteine residues can be used with good effect, providing for the facile intermolecular oxidation/reduction of the associated thiol functionalities.

Peptide components of this invention preferably comprise naturally-occurring amino acids. However, incorporation of known artificial amino acids such as beta or gamma amino acids and those containing non-natural side chains, and/or other similar monomers such as hydroxyacids are also contemplated, with the effect that the corresponding component is peptide-like in this respect. One example already tested includes an amino acid substituted with a thiophene moiety so that polymerization can produce electrically conductive and/or fluorescent materials. Accordingly, such artificial amino acids, hydroxyacids or related monomers can be used to meet the spacer, phosphorylation and/or intermolecular bonding objectives described above.

Various aspects of the present invention can be described with reference to the peptide amphiphile illustrated in FIG. 1, but consistent with broader aspects of this invention, other compounds and compositions can be prepared in accordance with this invention and used for the self-assembly of fibrous cylindrical micelles and corresponding nanostructures. See, Table 1, below.

TABLE 1

| PA | SEQ ID NO: | N-terminus | Peptide (N to C) | C-terminus |
|----|------------|------------|------------------|------------|
| 1  | 2          | C16        | CCCCGGGS(P)RGD   | H          |
| 2  | 3          | C16        | CCCCGGGS(P)      | H          |
| 3  | 4          | H          | CCCCGGGS(P)RGD   | H          |
| 4  | 5          | C10        | CCCCGGGS(P)RGD   | H          |
| 5  | 6          | C6         | CCCCGGGS(P)RGD   | H          |
| 6  | 7          | C10        | GGGS(P)RGD       | H          |
| 7  | 8          | C16        | GGGS(P)RGD       | H          |
| 8  | 9          | C16        | AAAAGGGS(P)RGD   | H          |
| 9  | 10         | C10        | AAAAGGGS(P)RGD   | H          |
| 10 | 11         | C16        | CCCCGGGS(P)KGE   | H          |
| 11 | 12         | C10        | AAAAGGGS(P)KGE   | H          |
| 12 | 13         | C16        | AAAAGGGS(P)KGE   | H          |
| 13 | 14         | C22        | CCCCGGGS(P)RGD   | H          |
| 14 | 15         | C16        | CCCCGGGSRGD      | H          |
| 15 | 16         | C16        | CCCCGGGEIKVAV    | H          |
| 16 | 17         | C16        | CCCCGGGS(P)RGDS  | H          |
| 17 | 18         | $C_n$      | LLLKK-X          | H          |
| 18 |            | $C_n$      | LSL-X            | H          |
| 19 | 19         | $C_n$      | LSLS-X           | H          |

Figure 7:
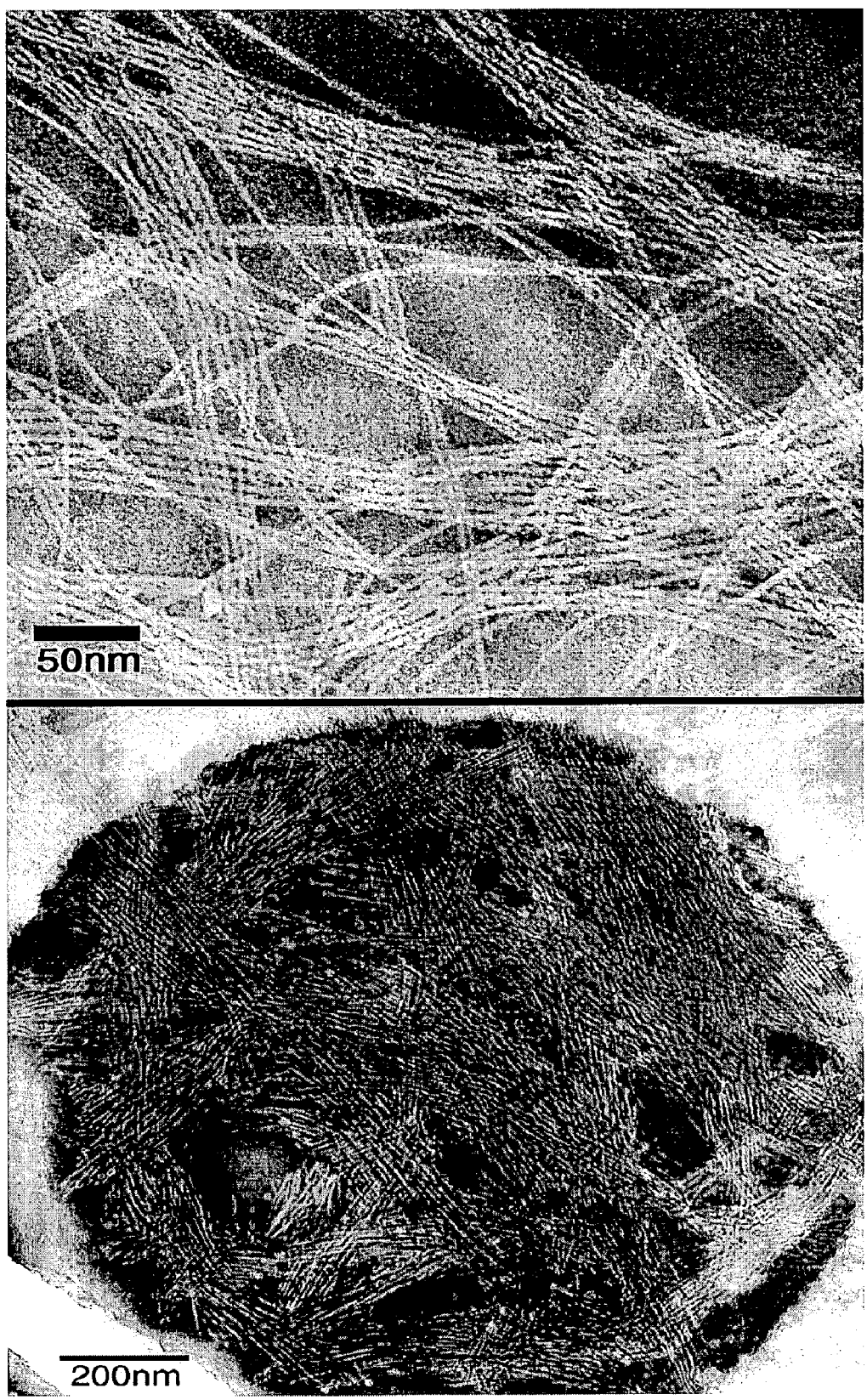
FIGS. 7-9. TEM micrographs for several cylindrical micelles prepared from PA molecules listed in Table 1. Specifically.
Figure 8:
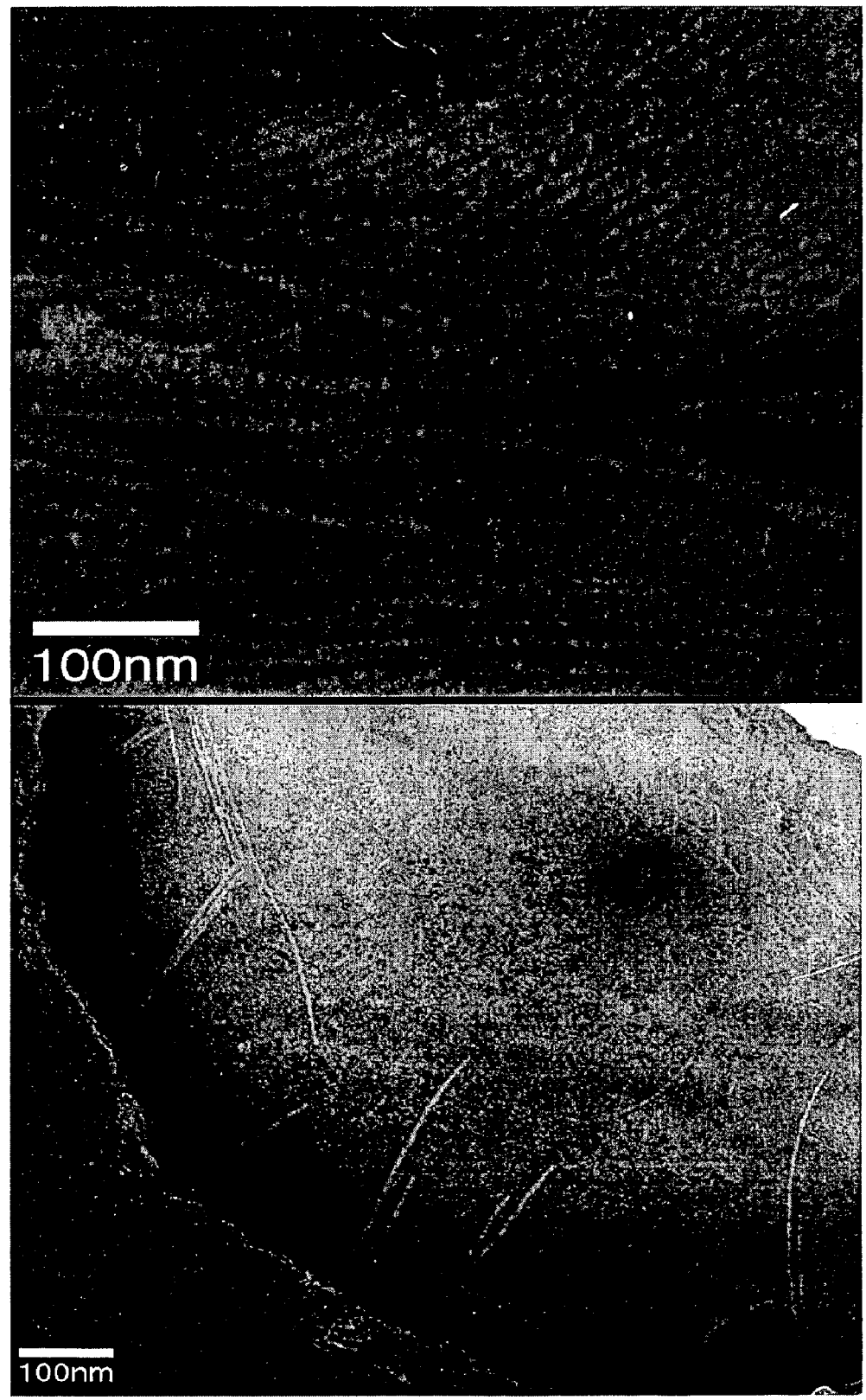
Figure 9:
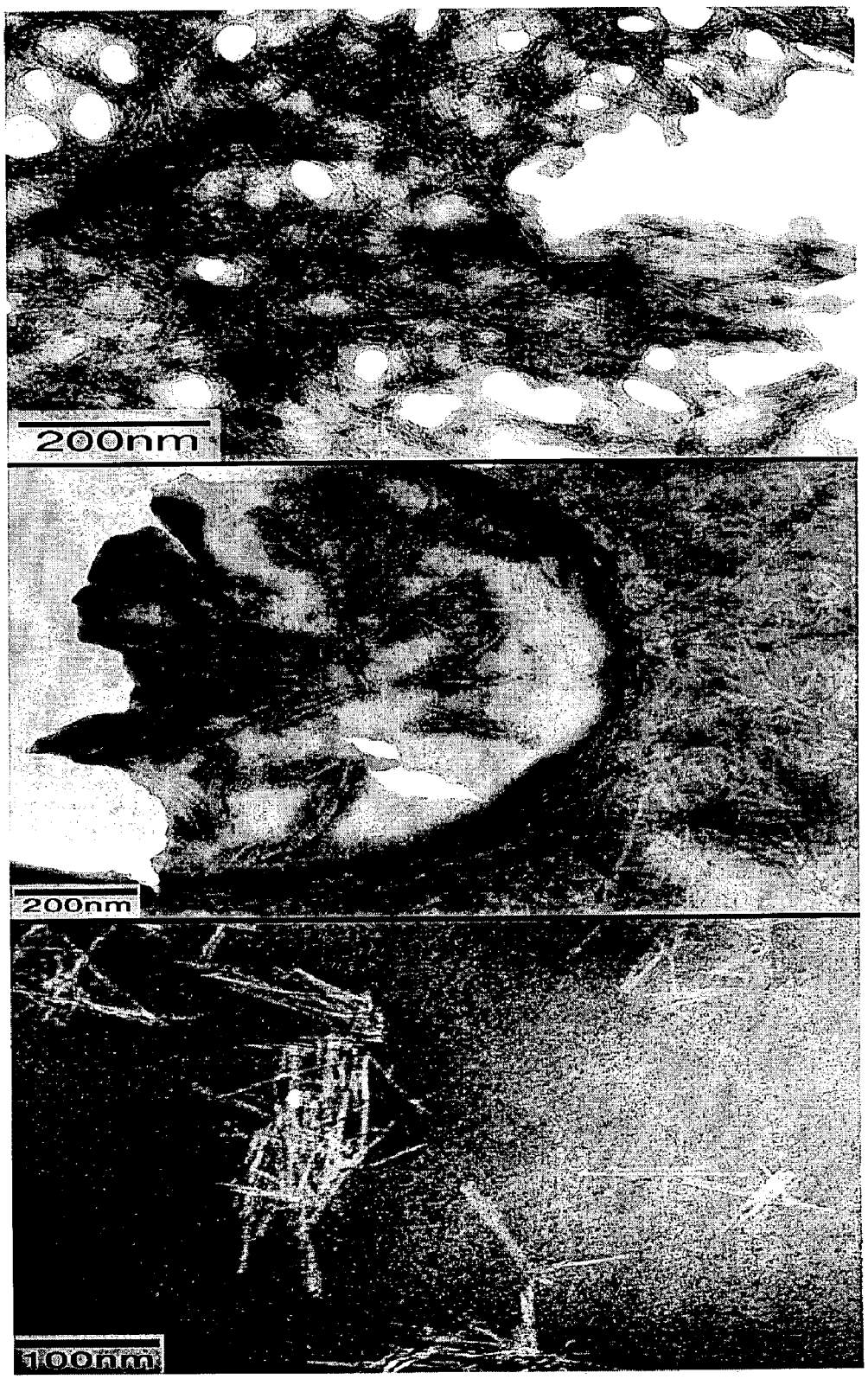

Depending upon desired cell or mineral growth, a phosphorylated moiety or residue may not be included (see PAs 14 and 15). As discussed above, cellular adhesion or other biointeraction may be promoted by a particular sequence of the peptide component. With reference to PAs 10-12 and 15, a non-RGD sequence can be utilized depending upon cellular target or end-use application. In particular, the IKVAV (SEQ ID NO: 1) sequence has been identified in other contexts as important for neuron growth and development. The YIGSR (SEQ ID NO: 20) sequence, as discussed more fully below, can also be used. Accordingly, the amphiphile compositions of this invention can include a peptide component having such a sequence for corresponding use. Other residues and/or bioactive epitope sequences capable of promoting cell adhesion, growth and/or development are known in the art and can be used in conjunction with the present invention, such as residues/sequences as can be incorporated into the peptide components and/or PA compositions of this invention using available synthetic techniques or straight-forward modifications thereof. With respect to drug delivery and related end-use applications, various bioactive epitope sequences incorporated into the PA compounds/compositions of this invention can be used to adsorb, bind and/or deliver a number of hydrophilic therapeutic agents, including but not limited to growth factors, related co-factors and/or activators. Conversely, such compound/compositions can be used to control the delivery rate of various hydrophobic/hydrocarbon therapeutic agents bound and/or encapsulated within the hydrophobic components thereof. With respect to Table 1, it is noted that several PA compounds/compositions do not include cysteine residues: while such a residue or peptide sequence can be used to enhance intermolecular nanofiber stability, it is not required for micelle formation in the first instance. Reference is made to FIGS. 7-9 for TEM micrographs of several PA compositions identified in Table 1.

Further reference is made to Table 1 and, in particular, PA compositions 17-19. Various other embodiments of this invention may comprise the residues shown, or where optionally X may further comprise one or more of the aforementioned residues as may be utilized for intramolecular structural flexibility, intermolecular stability, mineralization and/or cellular interaction. Accordingly, each such composition can optionally comprise, as desired for end-use application, one or more glycine, cysteine, phosphorylated and/or cell growth, development or adhesion residues. In accordance with the preceding discussion, the amphiphilic nature of such compositions provides for the presence of a suitably hydrophobic component $C_n$, where n is an integer corresponding to the number of carbon atoms in such a component sufficient to provide sufficient amphiphilic character and/or assembly structure. Without limitation, various embodiments of such compositions comprise a hydrophobic component (e.g., alkyl, biphenyl, cholesterol, etc.) of about $C_6$- about $C_{26}$. More specifically and without limitation, a sequence such as that provided by PA composition 17 (or as further comprising residue(s) X) can be utilized to modify and/or enhance the rate of nanostructure self-assembly. Likewise, without limitation, the sequences of PA compositions 18 and 19 (or as further comprising residue(s) X) can be used, as needed, to improve the structural or mechanical properties of the corresponding available nanostructured gel materials. Implementation of such peptides in the PA compositions of this invention do not, of course, preclude use of other residues. For example, PA compositions 17-19 can further comprise one or more glycine, cysteine, phosphorylated and/or cellular interaction residues, in accordance with this invention.

Figure 10B:
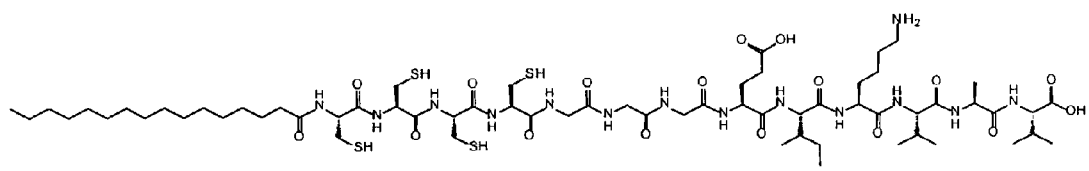
Figure 10B:
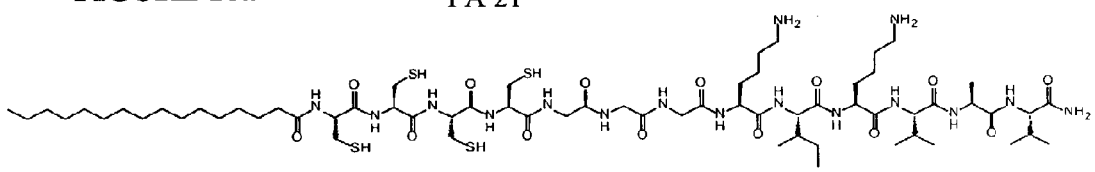

In part, the present invention also provides a sol-gel system including 1) a polar or aqueous solution and/or containing of one or more of the amphiphile compounds or compositions described herein, and 2) a factor or reagent sufficient to induce assembly, agglomeration of gelation under neutral or physiological conditions. Such gelation and/or self-assembly of various PA compositions into micellular nanofibers can be achieved under substantially neutral and/or physiological pH conditions through drying, introduction of a mono- or multivalent metal ion and/or the combination of differently charged amphiphiles. The approach of using differently charged amphiphiles can also be utilized to deliver in the self assembling nanofibrous system two or more bioactive molecules, each bearing different charges and this way combining the gelation technology with the delivery of multiple biological signals. Such facile factors, as described more fully below and in several of the following examples, can extend the sol-gel system and/or methodology of this invention to a variety of medical applications. These and other aspects of the present invention can be described with reference to the PA compositions provided in Table 2, below, with further reference to FIGS. 1, 10A-B and Table 1, above.

TABLE 2

| PA | SEQ ID NO: | N-terminus | Peptide (N to C) | C-terminus | Net Charge at pH 7 |
|---|---|---|---|---|---|
| 17 | 2 | C16 | CCCCGGGS(P)RGD | COOH | −3 |
| 18 | 9 | C16 | AAAAGGGS(P)RGD | COOH | −3 |
| 19 | 10 | C10 | AAAAGGGS(P)RGD | COOH | −3 |
| 20 | 15 | C16 | CCCCGGGSRGD | COOH | −1 |
| 21 | 16 | C16 | CCCCGGGEIKVAV | COOH | −1 |
| 22 | 21 | C16 | CCCCGGGKIKVAV | CONH$_2$ | +1 |
| 23 | 17 | C16 | CCCCGGGS(P)RGDS | COOH | −3 |
| 24 | 22 | C16 | AAAAGGGKYIGSR | CONH$_2$ | +2 |
| 25 | 23 | C16 | AAAAGGGEIKVAV | COOH | −1 |

The peptide epitopes on molecules 22-25 demonstrate the biomedical potential of the self assembling systems described here. RGD is the well known cell adhesion ligand found in fibronectin while IKVAV (SEQ ID NO: 1) and YIGSR (SEQ ID NO: 20) are laminin sequences known to interact with mammalian neurons. IKVAV (SEQ ID NO: 1) promotes neurite outgrowth in mammalian neurons, while YIGSR (SEQ ID NO: 20) plays a related role in neuronal cell-substrate adhesion. While these and other bioactive epitope sequences can be used to effect cell adhesion, proliferation or differentiation and related outcomes, in a broader context, the PA compounds/compositions and related methods of this invention can be used in conjunction with any epitope sequence capable of cellular interaction and/or binding to a cellular membrane receptor. In particular, peptide amphiphiles 23 and 25 have a net negative charge at neutral pH, whereas PAs 22 and 24 have a net positive charge. Electrostatically driven co-assembly between PA compounds 24 and 25 as well as 23 and 22 provide mixed nanofibers that simultaneously present two biological signals in a cellular environment.

Various peptide-amphiphile compositions are shown in Tables 1 and 2, but are provided only by way of illustrating one or more aspects of this invention. It will be understood by those skilled in the art that a range of other compositions are also contemplated. For example, the peptide components can be varied, limited only by functional considerations of the sort described herein. Accordingly, peptide length and/or sequence can be modified by variation in number or identity of amino acid or substituted monomer. Further, it will be understood that the C-terminus of any such sequence can be construed in light of an associated carboxylate functionality or derivative thereof. While the N-terminus of the peptides is illustrated with respect to the referenced conjugated hydrophobic and/or hydrocarbon components, it will be understood that such components can also be varied by length and/or composition, such variation limited only by the functional considerations presented herein. For example, a sixteen carbon (C16) component can comprise but is not limited to a straight-chain alkyl hydrocarbon. As would be understood by those skilled in the art, the structure and/or chemistry of such a component can be varied with regard to a particular, desired functionality of an amphiphile composition or assembly thereof. Likewise, the length of such a component is limited only by way of the degree of hydrophobicity desired for a particular amphiphile composition and/or assembled structure, in conjunction with a given solvent medium.

Figure 11:
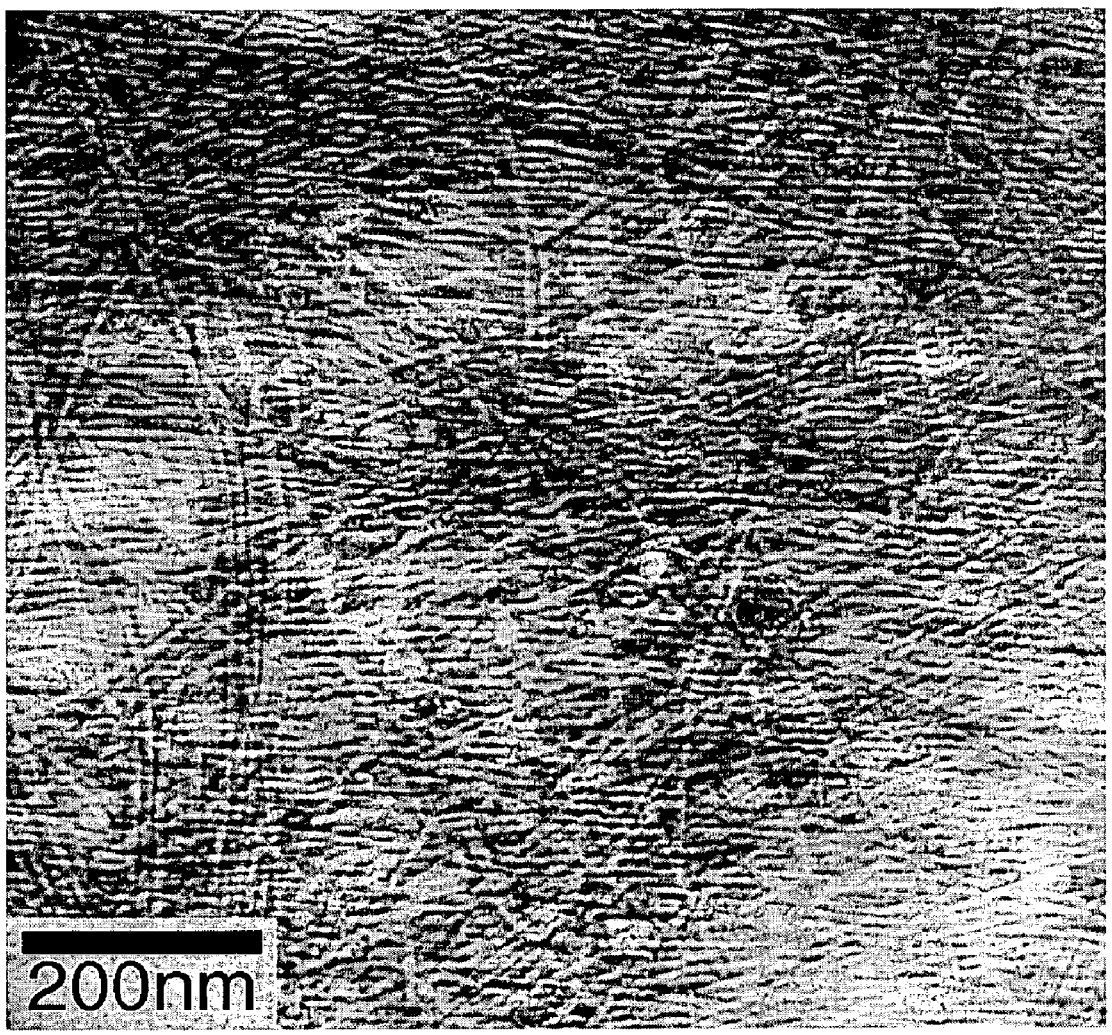
FIG. 11. Molecule 1 self-assemblies into nanofibers upon drying from a solution at physiological pH.

Consistent with broader aspects of this invention, it was found that representative peptide amphiphiles (for example, PAs 17-19 and 21, Table 2 and those of Table 1), when dissolved at neutral pH were dried onto surfaces, self-assembled into cylindrical micelles (FIG. 11). Such a facile approach allows this novel material to be formed in a pH independent manner, as may be important in applications that are particularly sensitive to changes in pH, including the delivery of cells in conjunction with the gelling system and generally avoiding contact between tissues and materials at non-physiological pH.

Figure 12:
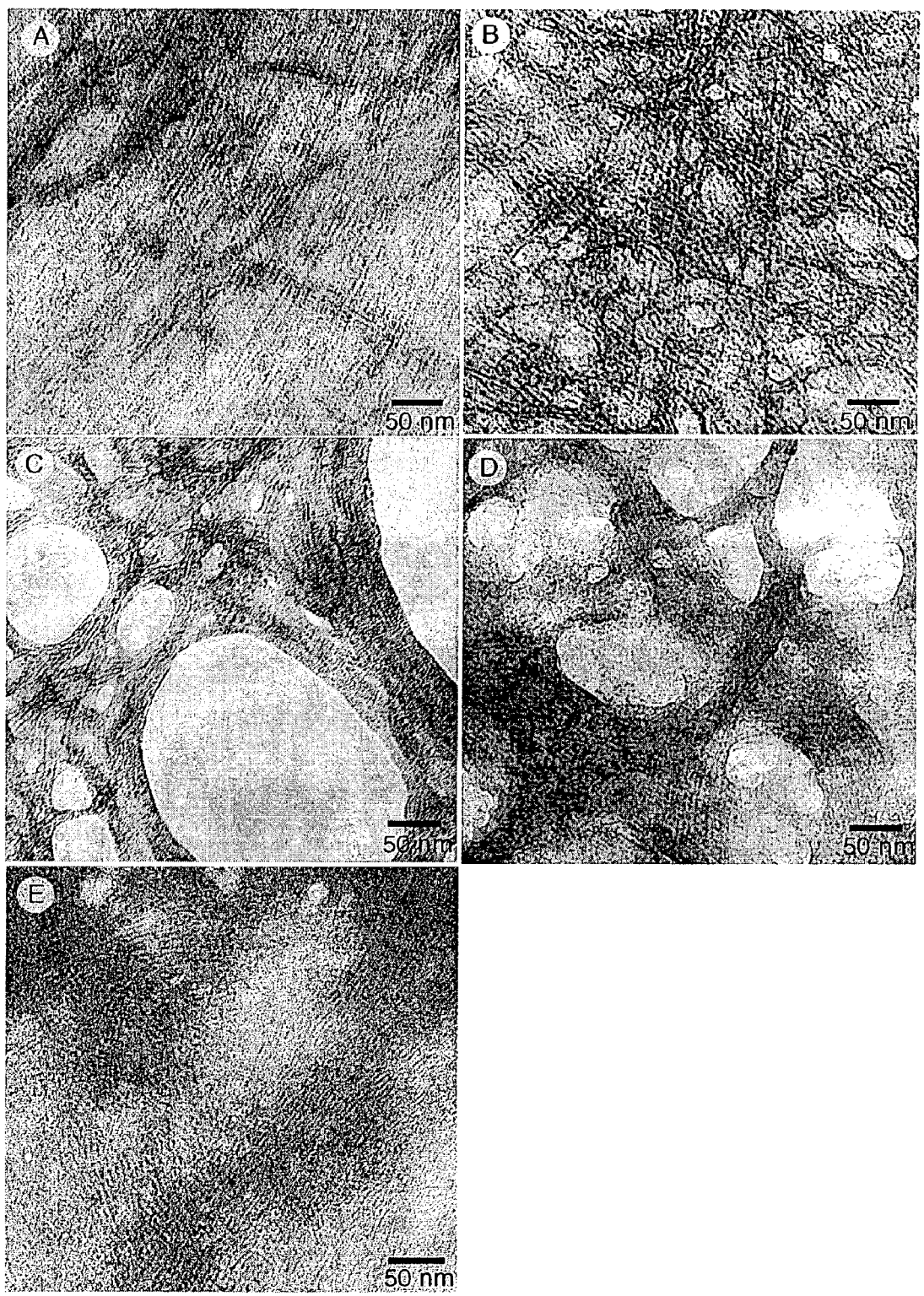
FIGS. 12A-12E. TEM micrographs of positively stained peptide-amphiphile gels formed by addition of: A) $Ca^{2+}$ to molecule 2 solution; B) $Cd^{2+}$ and molecule 2 solution; C) $Ca^{2+}$ to molecule 4 solution; D) $Fe^{2+}$ to molecule 1 solution; and E) $Zn^{2+}$ to molecule 1 solution.

Illustrating another such factor, the self-assembly of the PA molecules (for example, but not limited to PAs 17, 18 and 20, Table 2 and Table 3) into nanofibers can be induced by addition of metal ions such as, but not limited to $K^+$, $Ca^{+2}$, $Mg^{+2}$, $Cd^{+2}$, $Fe^{+2}$ and $Zn^{+2}$, and metal ions having higher oxidation states such as but not limited to the trivalent $Al^{+3}$ and $Fe^{+3}$. Self-supporting gels can be formed upon addition of a stoichiometric excess of such ions, preferably on the order of about 2-3 metal ions per molecule of PA. TEM study of these gels reveals a network of nanofibers that pack into flat bundles, similar to those found in the gels self-assembled by acidification (FIG. 12). (See examples 19a-c and Table 3, below.)

More generally, such PA compositions can be prepared with appropriate alkaline, alkaline earth, transitional metal salts or reagents comprising such salts. With further reference to Table 3, while negatively-charged PAs tend to gel in the presence of metal ions, gelation properties may vary depending upon PA composition and metal ion identity. Self-assembly and/or gelation can also be varied through modification of the hydrophobic and hydrophilic portions/regions of the PA compositions, one relative to the other. With regard to the hydrophilic region, choice of amino acid residues can affect gelation depending upon net charge of and/or charge distribution therein.

Figure 13:
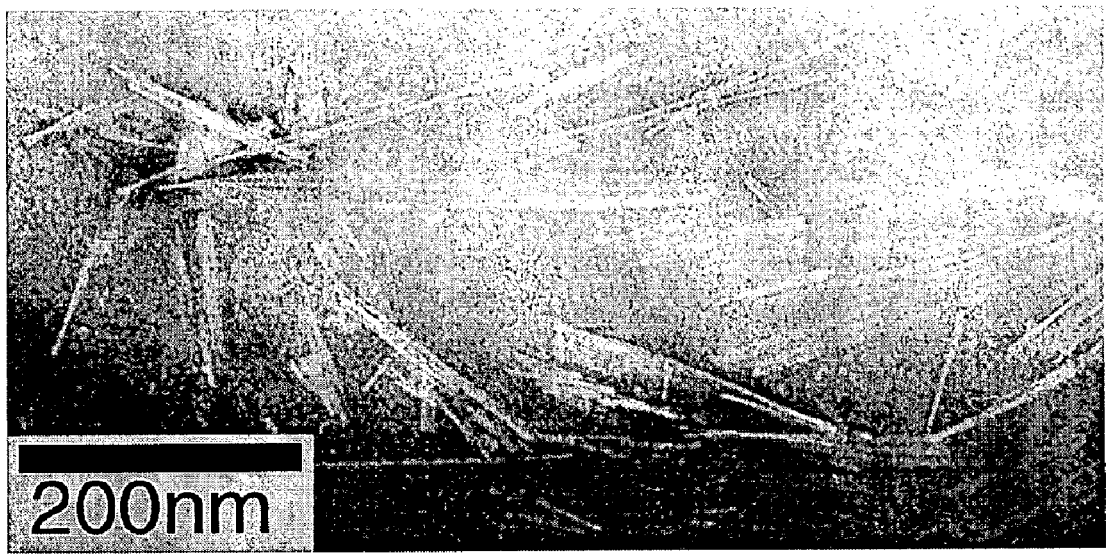
FIG. 13. Self-assembly induced by mixing two different peptide amphipiles (21 and 22) containing opposite charges.

As yet another factor inducing gelation under physiological conditions, consider two amphiphiles, such as but not limited to PAs 21 and 22 (Table 2), one having a net negative charge at neutral pH and one having a net positive charge at neutral pH—both dissolved at neutral pH. However, upon mixing such amphiphiles immediately form a gel. Examination by negative stain TEM shows the gel composed of cylindrical micelles (FIG. 13).

In one possible working model of the molecular organization of the mixed PA nanofibers, the hydrophobic alkyl tails are hidden in the center of the micelles with the more hydrophilic peptide segments of the molecules in contact with the aqueous environment. The cylindrical structure of this micelle could in part be explained by the tapered shape of individual molecules, but a second driving force might be beta sheet hydrogen bonding among peptide segments down the long axis of the fibers: the parallel β-sheet hydrogen bonding conformation is observed by FT-IR and on the unusual dominance of the cylindrical self-assembly motif across such a broad concentration range (<about 0.001% to >about 10% by weight). (See Example 9, below.)

Figures 14A, 14B, 14C:
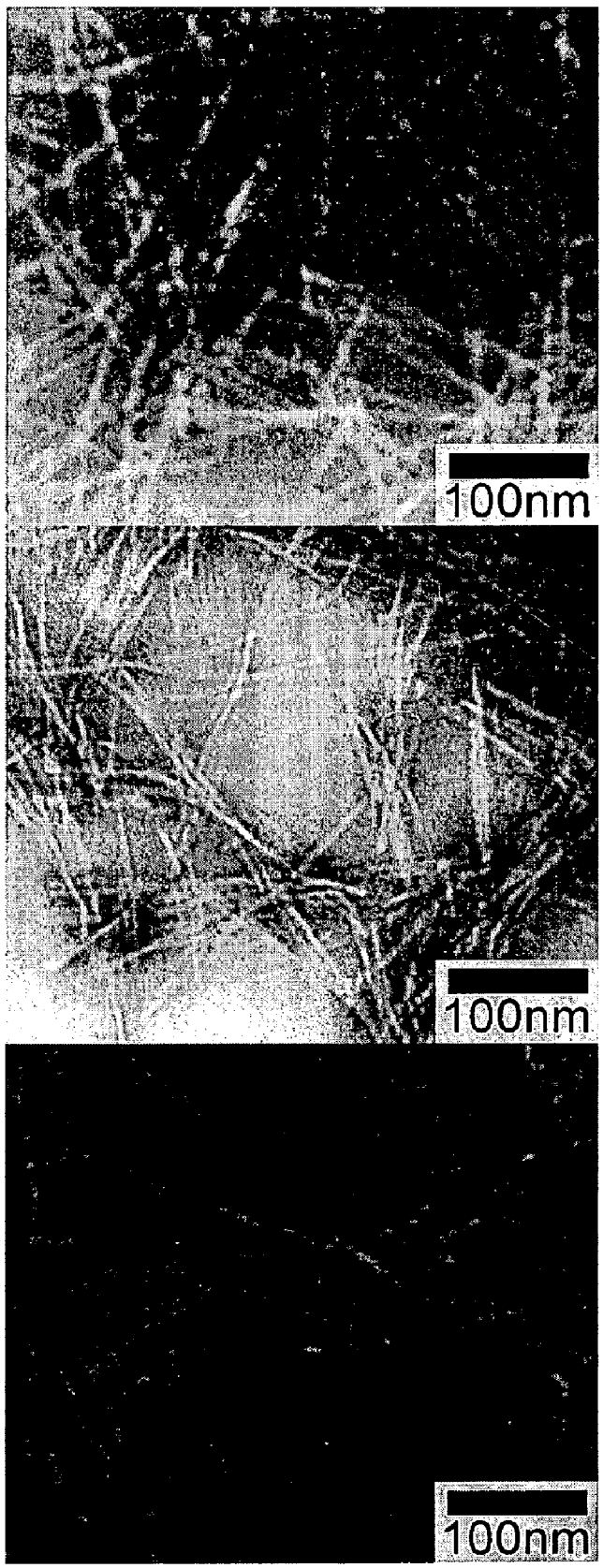
FIGS. 14A-C. TEM images of three different self-assembled peptide-amphiphile nanofibers. 14A: Negatively charged peptide amphiphile 25 assembled with acid. 14B: Positively charged 24 assembled with base. 14C: Nanofibers formed at neutral pH with a mixture of 24 and 25.

In the case of the mixed PA fibers, two oppositely charged molecules are believed thoroughly mixed within any given nanofiber as opposed to molecules segregating into mixtures of homomeric fibers. If homomeric fibers formed in spite of the highly unfavorable charge concentrations associated with these structures, it would be expected that the fibers pack into bundles of oppositely charged fibers in order to reduce electrostatic repulsion. However, the same amount or less bundling in the mixed PA fibers is observed as compared to fibers formed from a single PA molecule (FIG. 14).

Self-assembly and/or gelation under physiological conditions, as induced by the preceding factors, raise numerous implications regarding end use application and effect. Without limitation, with reference to the preceding, a binary or higher PA mixture makes available a sol-gel system for the formation of micellular nanofibers in a aqueous environment at neutral and/or physiological pH conditions. As discussed elsewhere herein, such a combination of two or more PA compounds can be used to assemble nanofibers with a range of residues providing a corresponding variety of concurrent chemical or biological signals for cell adhesion proliferation, differentiation and the like, yielding enhanced properties with regard to tissue engineering or regenerative applications. Alone, or in conjunction with one or more of the other factors discussed herein, it is contemplated that preferred medical or therapeutic embodiments of such a system or methodology can be implemented upon step-wise introduction and mixing of the subject PA compositions, with in situ gel formation.

Accordingly, such a system can be used in conjunction with a drug, medication or other therapeutic agent, as would be understood by those skilled in the art: the subject drug or therapeutic agent can be provided with or introduced to an appropriate aqueous or polar medium separately or in conjunction with one or more PA compounds. Introduction of a reagent and/or factor induces nanofiber assembly and/or gelation, incorporating such a drug/agent therein, if hydrophobic, or as bound to or sorbed on the surface thereof, if hydrophilic. Disassembly or solubilization of the nanofibrous network or gel can release or deliver the drug/agent as or where required. As would be understood by those skilled in the art made aware of this invention, a range of both hydrophobic and hydrophilic drugs/agents can be utilized herewith. In particular, with regard to the peptide epitopes thereof, hydrophilic growth factors, co-factors and/or activators can be adsorbed on, delivered with and/or released by the PA compounds/compositions of this invention.

In preferred embodiments, regardless of any such factor or physiological condition, the amphiphile composition(s) of such a system includes a peptide component having residues capable of intermolecular cross-linking. The thiol moieties of cysteine residues can be used for intermolecular disulfide bond formation through introduction of a suitable oxidizing agent. Conversely, such bonds can be cleaved by a reducing agent introduced to the system. The concentration of cysteine residues could be varied to control the chemical and biological stability of the nanofibrous system and therefore control the rate of drug or therapeutic delivery using the nanofibers as the carriers. Furthermore, enzymes could be incorporated in the nanofibers to control biodegradation rate through hydrolysis of the disulfide bonds. Such degradation and/or the concentration of cysteine residues can be utilized in a variety of tissue engineering contexts.

Corresponding to one or more preferred embodiments of such a material, composition or system, the present invention can also include a nanostructured template for mineral crystal and/or cellular growth. Such a template includes a micelle assembly of amphiphile composition(s) of the type described herein, wherein the peptide component thereof may include a residue or sequence capable of intermolecular bond formation. In preferred embodiments, as described above, cysteine residues can be used for intermolecular disulfide bond formation. Various other preferred embodiments can further include one or more phosphorylated residues to promote crystal growth and/or mineralization, depending upon a desired material or tissue target.

In the context of biomimetic hard material or tissue, the present invention can also include an organo-mineral composite having a nanostructured peptide amphiphile template with mineral crystals thereon. As described above, this aspect of the present invention can be illustrated with the present amphiphile compositions, assembled as nanostructured fibers, used to nucleate and grow hydroxyapatite crystals. In preferred embodiments, the amphiphilic compositions include peptide components having one or more residues promoting crystal nucleation and growth. Such preferred peptide components can also include one or more residues capable of intermolecular bonding to stabilize the nanofiber template. While this inventive aspect has been described in conjunction with hydroxyapatite nucleation and growth, the mineral component of this composite can include other inorganic compounds and/or oxides. Such residues, sequences or moieties are of the type described herein, or as would otherwise be understood by those skilled in the art made aware of this invention.

Regardless, the c-axes of the mineral crystals of such composites are aligned with the longitudinal fiber axes, in a manner analogous to the alignment observed between collagen fibrils and HA crystals in natural bone tissue. Accordingly, the present invention can also include a method of using a peptide amphiphile, in accordance with this invention, to promote and control HA crystal growth. The identity of the PA compositions used therewith is limited only by way of those structural considerations described elsewhere herein. Consistent therewith and with the broader aspects of this invention, such a method includes 1) providing an aqueous or other suitable polar medium of one or more peptide amphiphile compositions, 2) inducing assembly thereof into cylindrical micelle structures, 3) optimally stabilizing the structures with intermolecular bond formation, and 4) introducing to the medium reagents suitable for the preparation of HA and crystalline growth thereof on the nanofiber micelle structures.

As provided elsewhere herein, one or more amphiphile compositions can be used to provide fibers with a variety of cell adhesion, mineralization and/or structural capabilities. A combination of such compositions can be used to assemble a nanofibrous matrix with synergistic properties beneficial for a particular crystal and/or cellular development, such compositions as may vary according to peptide component, residue sequence, hydrophobic or hydrocarbon component and/or resulting PA compound or assembly configuration. As described elsewhere herein, a combination of charged PA compositions can be used to effect assembly—likewise with drying and incorporation of divalent cations.

EXAMPLES OF THE INVENTION

The following non-limiting examples and data illustrate various aspects and features relating to the compositions, micelles, composites and/or methods of the present invention, including self-assembly of a peptide-amphiphile nanofiber system, as is available through the methodologies described herein. In comparison with the prior art, the present structures, template designs and related methods provide results and data which are surprising, unexpected and contrary thereto. While the utility of this invention is illustrated through the use of several amphiphiles, biomimetic micelles and resulting organo-mineral composites, it will be understood by those skilled in the art that comparable results are obtainable with various other amphiphiles, nanofibers/micelles and/or composites, as are commensurate with the scope of this invention.

Example 1

Figure 2:
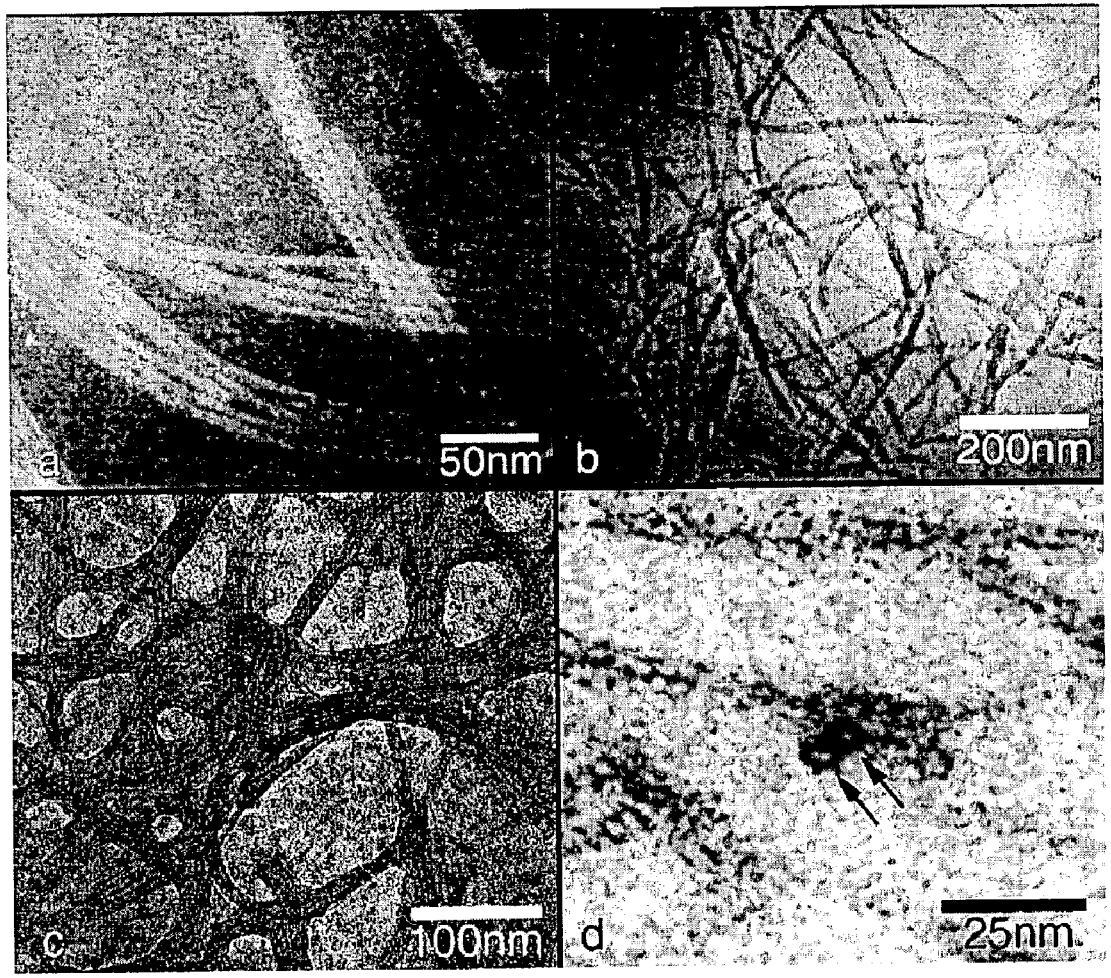
FIGS. 2a-2d. a) Negative stain (phosphotungstic acid) transmission electron microscopy (TEM) of self-assembled nanofibers before covalent capture. Fibers are arranged in ribbon-like parallel arrays. b) Vitreous ice cryo-TEM of the fibers reveals the diameter of the fibers in their native hydrated state to be 7.6±1 nm. c) Positive stain (uranyl acetate) TEM of the self-assembled nanofibers after oxidative cross-linking showing electron dense regions due to the stain that localized on the periphery of the fibers. d) Thin section TEM of positively stained (uranyl acetate) nanofibers after oxidative cross-linking and embedding in epoxy resin. Two fibers are observed in cross-section (arrows) clearly showing the lack of staining in the interior of the fiber.

After synthesis (see, example 10), the PA of FIG. 1 (characterized by $^1$H NMR and matrix-assisted laser desorption/ionization time-of-flight mass spectrometry (MALDI-TOF MS): matrix ion $[M-H]^{-1}=1333$) was treated with dithiothreitol (DTT) at a pH of 8 to reduce all cysteine residues to free thiols. At this pH the PA was found to be soluble in excess of 50 mg/ml in water. However, upon acidification of the solution below pH 4 the material rapidly becomes insoluble. Solutions more concentrated than 2.5 mg/ml form birefringent gels in water that are self-supporting upon inversion of the container. Examination of the gels by cryo-TEM, which preserves the native, hydrated state of the material, revealed a network of fibers with a diameter of 7.6±1 nm and lengths up to several microns (FIG. 2b). Negatives were digitized in the Umax PowerLook scanner with resolution 1200 dpi. The average thickness of the PA fibers was determined by two different procedures. First the Fourier transform of the images and following measurements of the distances between the peaks were performed in the NIH Image 1201.1262 program. The second approach applied was averaging technique based on the cross-correlation method, widely used in single particle reconstruction using the EMAN 1201.1202 program. For each data set 1200-1300 individual boxes were selected. (E. Beniash, W. Traub, A. Veis, S. Weiner, J. Struct. Biol. 132, 212-225 (2000). Positively and negatively stained dried fibers were found to have diameters of 6.0±1 nm (FIG. 2a, c). TEM using the positive stain uranyl acetate, which preferentially stains acidic groups, revealed increased electron density at the periphery of the fiber. (J. R. Harris, Ed. *Electron Microscopy in Biology, A Practical Approach*; Oxford University Press: New York, 1991). Additionally, gels that were stained, embedded in epoxy resin and sectioned for TEM, showed fibers in cross-section in which donut shaped patterns were observed indicating staining only on the outer portion of the fiber (FIG. 2d). The two positive staining experiments of this example indicate that the hydrophobic alkyl tails pack on the inside of the fiber and the acidic moieties of the peptide are displayed on the surface of the fiber.

Example 2

The formation of the fibers was found to be concentration independent over more than three orders of magnitude (0.01 mg/ml to 50 mg/ml), however a second level of hierarchy was observed that was concentration dependent. As the concentration of the PA was increased, a larger number of the fibers were observed to pack into flat ribbons of fibers (FIG. 2a,c).

Example 3

Examination of the self-assembled material by FT-IR revealed a bimodal amide I peak with maxima at 1658 cm$^{-1}$ (α-helix) and 1632 cm$^{-1}$ (β-sheet) along with a N—H stretching peak at 3287 cm$^{-1}$ indicating the formation of a hydrogen bonded structure, possibly utilizing a combination of β-sheet and α-helical secondary structure in the fibers (S. Krimm, J. Bandekar, *Adv. Protein Chem.* 38, 181-364 (1986); W. K. Surewicz, H. H. Mantsch, D. Chapman, *Biochemistry* 32, 389-394 (1993)). Based on the above data the nanofibers were modeled as cylindrical micelles in which the alkyl tails pack on the inside of the fiber and peptide segments are displayed on the outside containing both β-sheet and α-helical secondary structure. This model results in a fiber with a diameter of 8.5 nm, which is within the margin of error of our TEM measurements (FIG. 1c).

With reference to examples 4-9, the following abbreviations are employed for the reagents used. PA: peptide-amphiphile, TEM: transmission electron microscopy, DTT: dithiothreitol, EDT: ethanedithiol, TIS: triisopropyl silane, TFA: trifluoroacetic acid, HBTU: (2-(1 h-benzotriazole-1-yl)-1,1,3,3-tetramethyluronium hexafluorophosphate, DiEA: Diisopropylethylamine. Except as noted below, all chemicals were purchased from Fisher or Aldrich and used as provided. DiEA and Piperidine were redistilled before use. Amino acid derivatives, derivatized resins and HBTU were purchased from Nova Biochem. All water used was deionized with a Millipore Milli-Q water purifier operating at a resistance of 18 MΩ.

Example 4

With reference to examples 5-9, below, the peptide-amphiphiles of Table 2 were prepared on a 0.25 mmole scale using standard FMOC chemistry on an Applied Biosystems 733A automated peptide synthesizer. All peptides prepared have a C-terminal carboxylic acid and were made using prederivatized Wang resin. After the peptide portion of the molecule was prepared the resin was removed from the automated synthesizer and the N-terminus capped with a fatty acid containing 10 or 16 carbon atoms. The alkylation reaction was accomplished using 2 equivalents of the fatty acid, 2 equivalents HBTU and 6 equivalents of DiEA in DMF. The reaction was allowed to proceed for at least six hours after which the reaction was monitored by ninhydrin. The alkylation reaction was repeated until the ninhydrin test was negative. In general the longer the fatty acid the more repetitions were required to drive the reaction to completion.

Cleavage and deprotection of the peptide-amphiphiles containing cysteine was done with a mixture of TFA, water, TIS and EDT in a ratio of 91:3:3:3 for three hours at room temperature. The cleavage mixture and two subsequent TFA washings were filtered into a round bottom flask. The solution was roto-evaporated to a thick viscous solution. This solution was triturated with cold diethylether. The white precipitation was collected by filtration, washed with copious cold ether and dried under vacuum. Typically, 200 mg of the peptide-amphiphile powder was dissolved in 20 ml of water with the addition of 1M NaOH to adjust the pH of the solution to 8 and 200 mg of dithiothreitol (DTT) to reduce all cysteine amino acids to the free thiol and allowed to stir overnight. The solution was then filtered through a 0.2 µm nylon Acros filter into a new round bottom flask. This 10 mg/ml (1% by weight) solution was used for all subsequent manipulations. Work up of peptide-amphiphiles not containing cysteine were performed as above accept that ethanedithiol was omitted from the cleavage reaction and DTT was not used in the preparation of aqueous solutions. Peptide-amphiphiles were characterized by MALDI-TOF MS and were found to have the expected molecular weight.

Example 5

Nanofibers containing two different peptide-amphiphiles can be prepared as follows. Peptide-amphiphile 21 was dissolved in water at pH 7 at a concentration of 5 mg/ml. Peptide-amphiphile 22 was dissolved in water at pH 7 at a concentration of 5 mg/ml in a separate vial. Both solutions were slightly cloudy. Upon mixing the two solutions the material formed a gel in less then one second.

Example 6

Figure 10C:
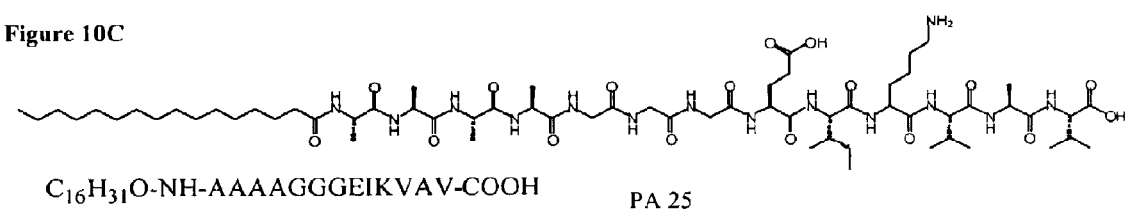
FIGS. 10C-E. Chemical structures of four peptide-amphiphiles used for self-assembly (SEQ ID NOS 23, 22 & 17 are disclosed respectively in order of appearance).
Figure 10D:
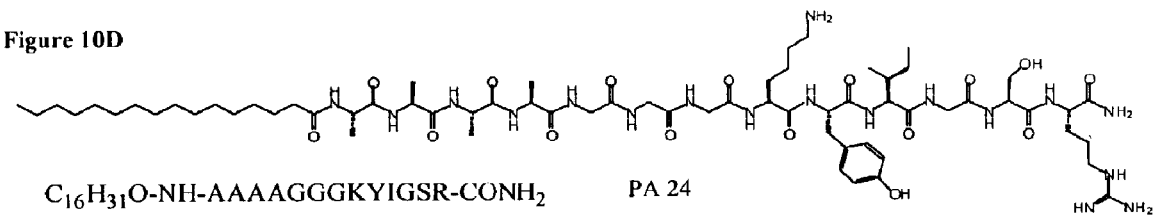
Figure 10E:
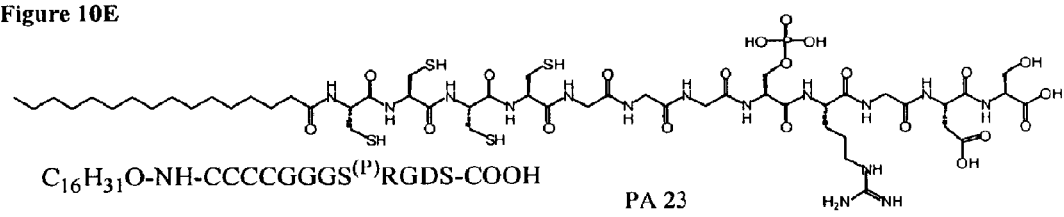

Several PAs with basic amino acids that can self-assemble at alkaline pH and also mixed systems, in which oppositely charged PAs self-assemble at neutral pH, were prepared. For this purpose PA compounds 22-25 were prepared by standard solid phase peptide synthesis followed by alkylation with the C16 fatty acid, palmitic acid. See Table 2, FIG. 10b (PA 22) and FIGS. 10c-e (PAs 23-25). The peptides thus prepared were characterized by electrospray mass spectroscopy and found to correspond to their respective expected masses. All four of the PAs were found to dissolve in water at neutral pH at concentrations of 1 mg/ml or less. Molecules 22 and 23 were fully reduced to eliminate disulfide bond crosslinking then used under anaerobic conditions or left in an excess of dithiothreitol. Compounds 24 and 25 could be dissolved at higher concentrations (10 mg/ml) but molecules 22 and 24 were cloudy and viscous at this concentration.

Example 7

Solutions of each compound of example 6 were prepared at a concentration of 0.1 mg/ml at neutral pH. Molecule 25 was slowly acidified (HCl) and found to precipitate below a pH of 4.5 while increasing the solution's pH (KOH) left the molecule completely dissolved. Conversely, base was slowly added to a solution of molecule 24 and it was found to be soluble until a pH above 9.5 was reached at which point a precipitate formed. At neutral pH both molecules were completely dissolved, however, upon mixing these clear solutions a precipitation formed within seconds with no significant change of pH. At higher concentrations (5 mg/ml) mixing the oppositely charged amphiphiles caused the immediate formation of a birefringent gel. Molecules 22 and 23, which can be covalently crosslinked through oxidation of their cysteine residues, behaved in a similar fashion.

Example 8

Samples of the precipitated material in each of the six solutions of examples 6-7, one for each individual PA compound and mixed samples of PAs 24 and 25 and PAs 22 and 23, were examined by negative stain transmission electron microscopy (TEM) and FT-IR. TEM revealed that in all cases the PA had self-assembled into nanofibers with nearly uniform diameters of 7 nm+/−1 nm, often many microns long.

Example 9

FT-IR spectra of the preceding solutions showed strong hydrogen bonding based on N—H stretching frequencies between 3276 and 3289 cm$^{-1}$, and all spectra showed significant parallel β sheet character based on the position of the amide I band at 1630 cm$^{-1}$. Additional contributions in this region between 1650 and 1680 cm$^{-1}$ indicate that the peptide region also adopts significant α-helix and random coil characteristics. The pH response of the PA compounds, their structure by TEM, and their IR spectra suggest, without limitation, a possible model of self-assembly: at neutral pH molecule 25 has a net negative charge of −1. This charge helps to keep the molecule solubilized through electrostatic repulsion of other negatively charged species despite the large hydrophobic bulk of its fatty acid tail. Similarly, molecule 24 has a net charge of +2 at neutral pH and is soluble. Self-assembly is initiated when these charges are eliminated, as in the pH driven self-assembly, or when the charges are attractive instead of repulsive as in the case when oppositely charged amphiphiles are mixed. The fact that the mixed self-assembly occurs at neutral pH where the individual molecules are soluble strongly suggests that the self-assembly is driven by an electrostatic attraction involving both positively and negatively charged molecules and not simply hydrophobic collapse involving one or the other PA.

Example 10

100 μl of 10 mg/ml solution of peptide-amphiphile 20 was treated with 1M CaCl$_2$ (adjusted to pH 6) drop wise in 1 μl increments. The solutions were shaken after each addition of the CaCl$_2$ solution in order to obtain better diffusion of the divalent metal ions. Gelation was immediate. When examined by positive stain TEM the gel formed with calcium ions was found to be composed of nanofibers with the same dimensions as those formed by acid induced self-assembly and by surface drying. This calcium induced self-assembly may be particularly useful for medical applications where formation of a gel at physiological pH is desired. Trivalent metal cations can also be used for gelation.

Example 11

To demonstrate cross-linking, in accordance with this invention, the gels formed above (examples 5 and 6) were treated with 0.05M I$_2$ which was adjusted to a pH of 3.5. The iodine solution was placed on top of the gel and allowed to slowly diffuse into the gel. After the iodine color had completely penetrated the gel, excess iodine was removed. The gel was then soaked in a bath of deionized water which was periodically changed until the discoloration from the iodine was gone as judged by eye (roughly 48 hours depending on the size of the gel).

Example 12

Illustrating another gelation factor of this invention, self-assembly can occur by simply taking a PA (such as PA 17, Table 2) or a combination of PAs dissolved in water at pH 8 and placing it on a surface which is allowed to dry (for example, directly on a carbon coated TEM grid). Upon examination of this preparation by negative stain TEM we observed clearly the formation of nanofibers. (See, FIG. 11.)

Example 13

Samples of the peptide-amphiphiles were prepared for TEM analysis in two different ways. In some cases a small sample of the gel, prepared in bulk as described above, was smeared onto a holey carbon coated TEM grid (Quantifoil). Other samples were prepared directly on the grid by placing 10 ul of 0.01-0.02% solution of PA directly on the grid. The grid was then placed into a sealed chamber with HCl vapors for 10 minutes after which the grids were washed with de-ionized water. Two routine staining techniques, negative staining with PTA (phosphotungstic acid) or positive staining with uranyl acetate, were used in this study [Harris, 1991]. In all cases electron microscopy was performed at an accelerating voltage of 200 kV. (See, FIGS. 10-13).

Example 14

Figure 3:
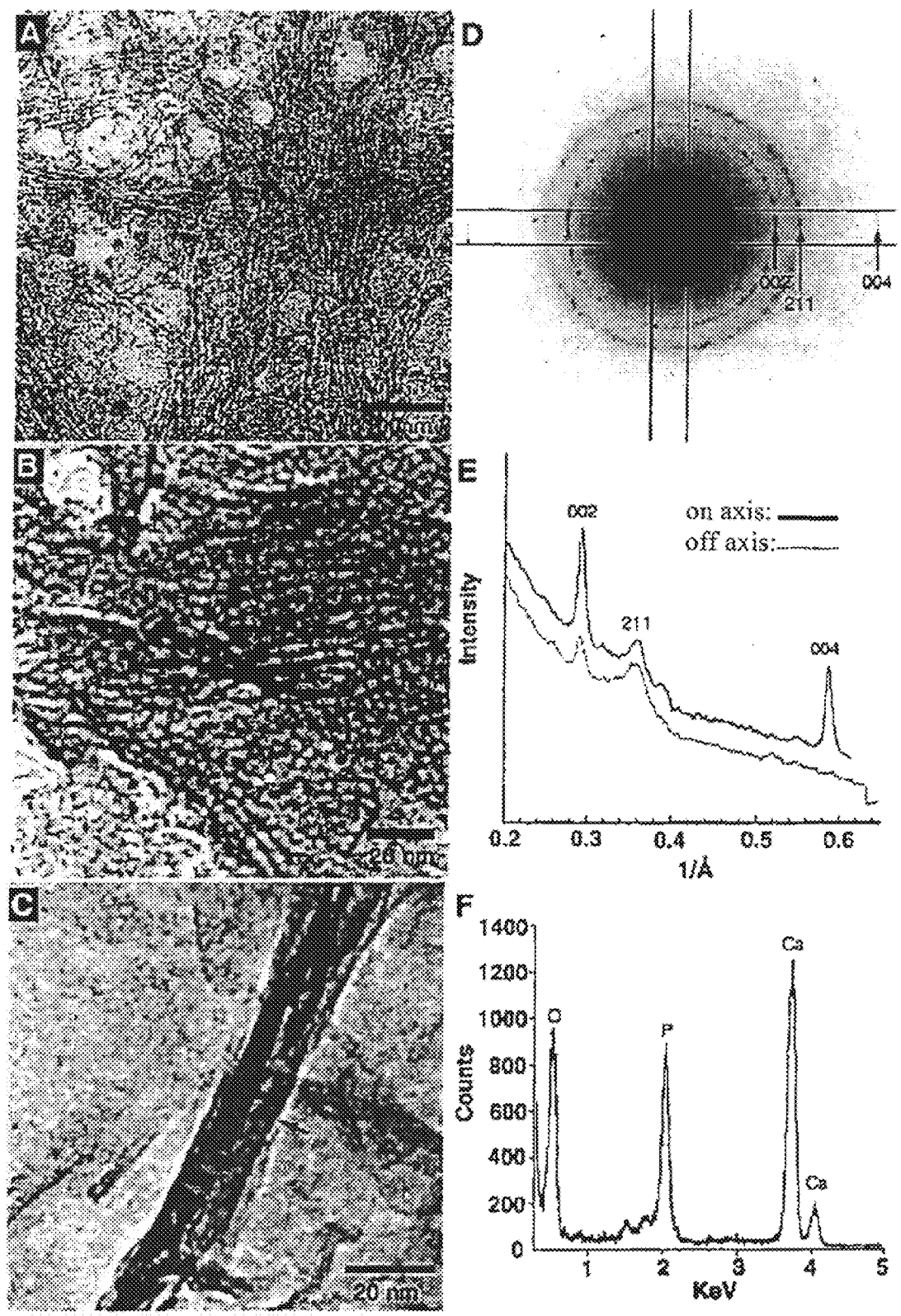
FIGS. 3a-3f. a) TEM micrographs of the unstained, cross-linked peptide-amphiphile fibers incubated for 10 min in CaCl$_2$ and Na$_2$HPO$_4$ solution. The fibers arranged in bundles are visible due to the high concentration of inorganic ions on their surface. b) After 20 minutes forming HA crystals (arrows) are observed in parallel arrays on some of the PA fibers. c) After 30 minutes mature HA crystals (arrows) completely cover the PA fibers. d) Electron diffraction pattern taken from a mineralized bundle of PA fibers after 30 minutes of exposure to calcium and phosphate. The presence and orientation of the diffraction arcs corresponding to the 002 and 004 planes indicate preferential alignment of the crystals with their c-axes along the long axis of the bundle. e) Plot of intensity versus inverse angstroms reveals that the 002 and 004 peaks of hydroxyapatite are strongly enhanced along the peptide-amphiphile fiber axis. f) Energy dispersive X-ray spectroscopy (EDS) profile of mineral crystals after 30 minutes of incubation reveals a Ca/P ratio of 1.67+/−0.08 as expected for HA.
Figure 5:
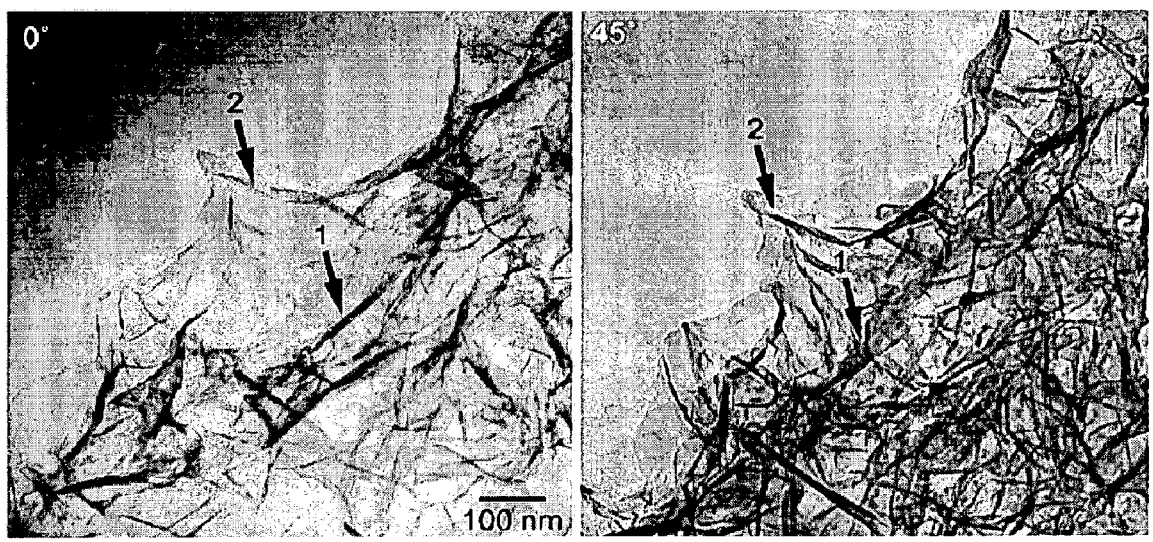
FIG. 5. A tilt pair taken from mineralized PA fibers after 30 minutes of incubation with calcium and phosphate demonstrating the plate shape of the crystals. The crystals that were "edge-on" (electron dense, narrow objects) in the zero degree image lose contrast in the 45 degree rotated image (arrow 1) while the contrast of the crystals that were "face-on" in the zero degree images increase (arrow 2).

To investigate the mineralization properties of PA nanofibers of this invention, the material was assembled and mineralized directly on a holey carbon coated TEM grid—to allow study of the dynamics of the mineralization process while minimizing artifacts of TEM sample preparation. To prepare samples, a drop of aqueous PA (1 mg/ml) was mounted on the holey grid and the self-assembly of the PA was induced in an atmosphere of HCl vapor. The grids were immersed in aqueous iodine to oxidize the cysteine thiol groups to disulfides. After rinsing with distilled water, the PA coated grids were treated with 5 μl of 10 mM $CaCl_2$ on one side and 5 μl of 5 mM $Na_2HPO_4$ on the other side. The two solutions are able to mix only by passing through the holes in the carbon support. Grids were examined by TEM at different time intervals (FIG. 3) and after 10 minutes inorganic material was observed to be concentrated around the fibers thus increasing their contrast (a crystalline phase was not detected at this time by electron diffraction). At 20 minutes the fibers begin to be covered with crystalline mineral, although significant amourphous material remains. After 30 minutes plate shaped polycrystalline mineral is visible throughout the surface of the fibers (FIG. 3C and FIG. 5). The mineral was analyzed by EDS (Energy Dispersion X-Ray Fluorescence Spectroscopy) which revealed a Ca/P ratio of 1.67.+−.0.08 which is consistent with the formation of HA with a formula of $Ca_{10}(PO_4)_6(OH)_2$ (FIG. 3f).

Example 15

Figure 6:
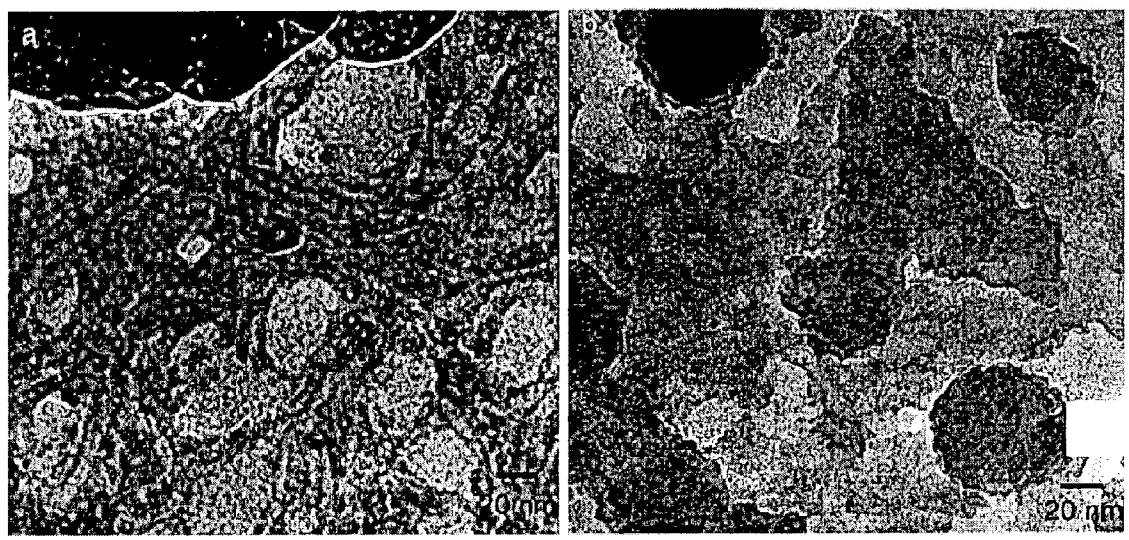
FIGS. 6a-6b. a) Nonphosphorylated PA fibers after 20 minutes of incubation with calcium and phosphate shows only amorphous mineral deposit concentrate on the fibers. b) Nonphosphorylated PA after 30 minutes of incubation with calcium and phosphate continue to show only amorphous mineral in contrast with phosphorylated PA which shows heavy crystallization at this time point.

As controls for the experiment of example 6, carbon coated TEM grids were treated as above but without PA fibers. In this case no mineral deposit was found on the grids. In a second control, a PA was prepared in which phosphoserine was replaced by serine and treated as above with calcium and phosphate. The nonphosphorylated fibers were observed by TEM after 20 and 30 minutes of incubation and in both cases an amorphous mineral deposit around the fibers was observed, but crystals did not form within this time frame (FIG. 6).

Example 16

In order to discern the relative orientation of the HA crystals with respect to PA fibers, several samples of example 6, in which isolated mineralized bundles of PA fibers could be observed, were analyzed by electron diffraction. In all cases preferential alignment of the HA crystallographic c-axis with the PA fiber long axis was observed. (FIG. 3D,E).

Example 17

Figure 4:
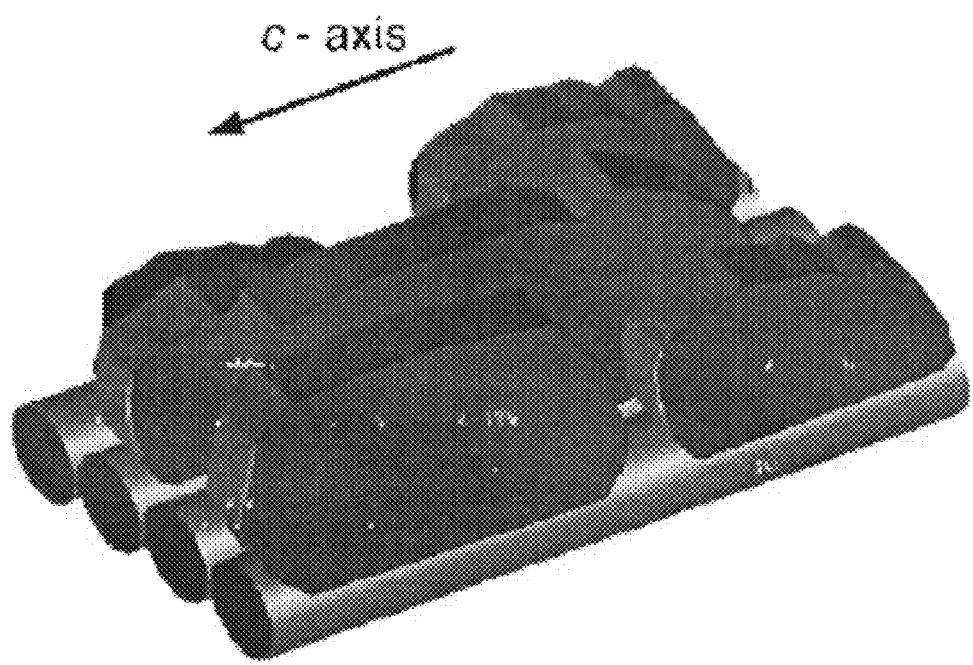
FIG. 4. Scheme showing possible relationships between peptide-amphiphile fibers and hydroxyapatite crystals in the mineralized bundle. Arrow indicates the direction of the c-axes of the crystals.

Mineralization experiments show that PA fibers of this invention are able to nucleate hydroxyapatite on their surfaces. Negatively charged surfaces can promote mineralization by establishing local ion supersaturation (S. Weiner, L. Addadi, *J. Mater. Chem.* 7, 689-702 (1997)). Particularly, the two acidic aminoacids phosphoserine and aspartic acid used here are abundant in the proteins of mineralized tissues proven to initiate crystal growth (L. Addadi, S. Weiner, *Proc. Nail. Acad. Sci.* 82, 4110-4114 (1985); G. Falini, S. Albeck, S. Weiner, L. Addadi, *Science* 271, 67-69 (1996); A. George, L. Bannon, B. Sabsay, J. W. Dillon, J. Malone, A. Veis, N. A. Jenkins, D. J. Gilbert, N. G. Copeland, *J. Biol. Chem.* 271, 32869-32873 (1996); S. Weiner, L. Addadi, *J. Mater. Chem.* 7, 689-702 (1997)). The fact that the fibers gain extra electron density prior to formation of the crystalline phase suggests the above mechanism may be utilized in our system. More surprising is the observation that the c-axes of the HA crystals are co-aligned with long axes of the fibers (FIG. 4). This fact implies that the orientation of crystalline nuclei and the subsequent crystal growth are not random but are controlled by the PA micelles. The exact mechanism of this control is not clear, however in similar systems such control is gained by specific arrangement of acidic groups that promote growth of the crystals in a particular orientation by an epitaxial mechanism (S. Mann, J. P. Hannington, R. J. P. Williams, *Nature* 324, 565-567 (1986); S. Weiner, L. Addadi, *J. Mater. Chem.* 7, 689-702 (1997); J. Aizenberg, A. J. Black, G. M. Whitesides, *Nature* 398, 495-498 (1999)). An analogous mechanism may be employed with PA fibers. Previous in vitro studies showing oriented crystal growth from organic templates were done mainly in two dimensional systems. The results of this example show for the first time oriented crystal growth in a synthetic fibrous organic substrate.

Example 18

Several additional representative peptide-amphiphiles of this invention were prepared by manual solid phase peptide synthesis starting from 0.5 mmoles of an FMOC-Asp(tBu)-WANG resin. Deprotection of the initial and subsequent FMOC groups and was accomplished by double treatment with 15 ml of 30% piperidine in DMF for 2 minutes and 7 minutes. The resin was then washed with 15 ml of DMF 5 times. With the exception of cysteine derivatives, amino acids (4 equivalents) were preactivated with HBTU (3.95 equivalents) and DiEA (6 equivalents) in 10 ml of DMF for two minutes. The activated solution was then added to the deprotected resin and allowed to shake for 30 minutes after which a small sample was removed and analyzed with ninhydrin to test for completeness of the reaction. Failed reactions were recoupled in an identical fashion. Cysteine was coupled via the FMOC-Cys(Trt)-OPfp activated ester with the addition of 1 equivalent of DiEA in order to avoid suspected epimerization found using the standard FMOC-Cys(ACM)-OH derivative with the conditions described above. Other amino acid derivatives used included FMOC-Gly-OH, FMOC-Arg(Pbf)-OH and FMOC-Ser(PO(OBzl)OH)—OH. Analogous derivatives available in the art may be used to couple A, S, L, K and other such residues, including those shown in Tables 1 and 2. The corresponding protecting groups and associated chemistries are known in the art and may vary depending upon the subject amino acid residue. The final step was coupling of a fatty acid (palmitic acid) and was accomplished using 2 equivalents of the acid activated with 2 equivalent of HBTU and 3 equivalents of DiEA in 15 ml DMF for 2 minutes. The solution was allowed to react with the resin overnight. Likewise, other reagents and starting materials of the sort useful in the preparation of the inventive compositions, but not limited to those shown in Tables 1 and 2, are readily-available and known to those skilled in the art, such reagents/starting materials as may be used for the hydrophobic/hydrocarbon and peptide (residues/monomers) components.

Cleavage and deprotection of the peptide-amphiphiles was done with a mixture of TFA, water, triisopropyl silane (TIS) and ethane dithiol (EDT) in a ratio of 91:3:3:3 for three hours at room temperature. The cleavage mixture and TFA washings were filtered into a round bottom flask. The solution was roto-evaporated and then redissolved in a minimum of neat TFA. This solution was triturated with cold diethylether. The white precipitation was collected by filtration and dried under vacuum.

Example 19a

To determine the relative number of metal ions necessary for gelation of the PAs, titration experiments were performed with PA molecules 26 and 27. These tests show that the minimal amount of $Ca^{+2}$ and $Gd^{+3}$ ions needed for the gelation is or about equal to the number of PA molecules in solution. (See Table 3, below). PAs positively charged without containing negatively charged functional groups did not gel upon addition of metal salts. None of the negatively charged peptide-amphiphiles except molecule 32 formed gels in the presence of KCl at a ratio 1 molecule of PA per 20 molecules of KCl. Further tests on the gelation abilities of monovalent salts showed that 10 mM solutions of compounds 26 and 27 did not gel in the presence of KCl or NaCl at concentrations up to 6M. In contrast to other PAs, an addition of 200 mM of KCl to 10 mM solution of molecules 32 and 33 caused formation of a self-supporting gel.

Example 19b

An additional factor in self-assembly may be exemplified by the structure of PAs 32 and 33. Both these molecules contain the IKVAV (SEQ ID NO: 1) sequence at the c-terminus of the peptide segment. This sequence is comprised is of alternating extremely hydrophobic amino acids I and V and more hydrophilic ones such as A, and K. Since the side chains of adjacent amino acids are located on opposite sides of the peptide backbone this sequence is, itself, amphiphilic. As such, PAs 32 and 33 may be considered as double or two dimensional amphiphiles, with one axis of amphiphilicity coinciding with the backbone of the molecule and amphiphilic peptide segment at the c-terminus, in addition to hydrophobic interactions between the alkyl moieties of the molecules.

Example 19c

The gels formed by addition of metal ions are remarkably stable. Such experiments show that they endure very basic conditions up to pH 11, and are stable at pH as low as 4. The gels also survive heating up to 100° C., though they slightly shrink. The gels also remain intact when exposed to a volume of deionized water 10 times greater than the volume of the gel for several days without any visible changes.

Example 20a

When $Cu(ClO_4)_2$ was added to the PA solutions the samples changed from transparent to blue upon gelation. The aqueous solution of copper perchlorate at same concentration was completely transparent. UV-Vis analysis of the gels of molecules 27 and 28 shows significant shift in absorbance compare to the aqueous solution of $Cu(ClO_4)_2$ of same concentration. These results are suggestive of formation of metal PA complexes upon gelation.

Example 20b

A significant absorbance shift in the ultraviolet-visible spectroscopy (UV-vis spectra) of $Cu^{+2}$ induced gels, compared to aqueous solution of $Cu(ClO_4)_2$, implies formation of the metal-PA complexes. The disappearance of the peak at 1730 $cm^{-1}$ accompanied by decreasing of the depth of minimum between Amide I and Amide II bands in the spectra of metal induced gels hints on the formation of metal-carboxyl ionic bonds. Also, the strength of the polyvalent metal ion induced gels in comparison to the pH driven self-assemblies under wide variety of conditions suggests presence of relatively strong bonds between PA molecules.

TABLE 3

Peptide-amphiphiles and their gelation properties.

| | PA | KCl*** | $MgCl_2$ | $CaCl_2$ | $BaCl_2$ | $Cu(ClO_4)_2$ | $ZnBr_2$ | $GdCl_3$ | SEQ ID NO: |
|---|---|---|---|---|---|---|---|---|---|
| 26 | Alkyl*-$C_4G_3S^{(P)}$RGD-COOH (−3)** | Liquid | weak gel | gel | gel | no data | gel | gel | 2 |
| 27 | Alkyl-$A_4G_3S^{(P)}$RGD-COOH (−3) | Liquid | weak gel | gel | gel | gel | gel | gel | 9 |
| 28 | Alkyl-$A_4G_3S^{(P)}$KGE-COOH (−3) | Liquid | Viscous liquid | gel | gel | no data | gel | gel | 12 |
| 29 | Alkyl-$C_4G_3$SRGD-COOH (−1) | Liquid | Cloudy liquid | gel | gel | no data | gel | gel | 15 |
| 30 | Alkyl-$A_3G_2$EQS—COOH (−2) | Liquid | gel | gel | gel | gel | gel | gel | 24 |
| 31 | Alkyl-$A_4G_3$ERGDS—COOH (−2) | liquid | Cloudy liquid | cloudy liquid | cloudy liquid | no data | gel | gel | 25 |
| 32 | Alkyl-$C_4G_3$EIKVAV—COOH (−1) | gel | gel | gel | no data | no data | gel | gel | 16 |
| 33 | Alkyl-$C_4G_3$KIKVAV—$NH_2$ (+2) | weak gel | Viscous liquid | viscous liquid | viscous liquid | no data | viscous liquid | viscous liquid | 21 |

*$C_{16}$ alkyl moieties (as tested) or about $C_6$ - about $C_{26}$ as referenced elsewhere herein.
**Overall charge of the molecule.
***KCl concentration was 200 mM for all molecules except molecules 26 and 27 that were examined at KCl concentration up to 6 M. Other salts concentrations were 20 mM. Concentration of the peptide amphiphiles in all cases was 10 mg/ml (roughly 8 mM).

Example 21

One potential application of the peptide-amphiphile self-assembled gels is in the area of tissue engineering, in particular the formation of artificial extracellular matrices and cell delivery systems. The results of this example show PA self-assembly in situ and in vitro cell culture systems. Body fluids as well as cell culture media contain significant amounts inorganic cations. It was presumed that the peptide amphiphiles would form a gel upon mixing with these liquids. Indeed, gel formation was observed when 10 mM solutions of PAs 27, 28 or 33 in water were mixed with equal amounts of cell culture media. Solutions of PA 27 and 28 were mixed with PBS and Hank's solutions depleted by $Ca^{2+}$ and $Mg^{2+}$, and no gel formation was observed—showing that multivalent metal ions present in the cell culture media induce self-assembly of negatively charged PAs in a cell culture medium.

Example 22a

TEM studies revealed the ultrastructural organization of metal ion induced PA gels. The electron micrographs of positively stained samples and resin embedded section show that the gels are comprised of 3-dimensional network of fibrils 5-6 nm in diameter, consistent with other measurements of dehydrated nanofibers (hydrated fibrils can be ~7.6 nm in diameter). The analysis of TEM data of positively stained material reveals that the uranyl acetate stains only peripheral parts of the fibrils, whereas the core remains unstained. The TEM of the resin embedded gel sections shows the same organization. It is apparent from the micrographs that the fibrils sectioned transversely have a doughnut appearance, with unstained central part and intensively stained outer circle. Since the uranyl acetate stains mainly charged groups and does not react with saturated hydrocarbons, these TEM results suggest that in the presence of polyvalent metal ions PA assemble into cylindrical micelles with their aliphatic tails in the core and the peptide parts comprising exterior layer. This structural organization of the PA nanofibers is similar to nanofibers assembled by a pH induced mechanism.

Example 22b

For TEM studies, positively stained samples of the PA gels were prepared as follows: The small amounts of the gels were mounted on the TEM grid and briefly dipped into deionized water in order to remove the excess of the material. The grids then were blotted against filter paper and placed on droplets of 2% uranyl acetate (EMS) aqueous solution. The samples were stained for 30-40 min in the dark. The grids then were washed in deionized water and dried. The samples were studied in the Hitachi 8100 high resolution TEM at acceleration voltage 200 kV.

For resin embedding, the gels were fixed in 2% glutar aldehyde aqueous solution (EMS). Samples then were washed in deionized water and stained with 2% aqueous uranyl acetate. The samples were dehydrated in ethanol gradient followed by propylene oxide. The samples then were transferred into 1:1 mixture of propylene oxide and epoxy resin (SPIpon, SPI). After 1 day of incubation the samples were transferred into pure epoxy resin. The resin was changed twice in 6 hours, The samples were polymerized for a day at 50° C. then at 60° C. for another day and at 70° C. for two more days. Thin sections of the samples were cut using Leica Ultracut. The samples were studied in the JEOL 100C TEM at acceleration voltage 100 kV.

Example 23a

FT-IR spectroscopy was employed to analyze interactions between the PA molecules in the fibrils. The Amide I band maxima of the PA gel samples, prepared by addition of metal ions, was located at 1630-1640 $cm^{-1}$. The position of Amide I band maximum in this region suggests that the peptide segments of the molecules adopt β-sheet conformation. In all the spectra studied no secondary peak at 1690 $cm^{-1}$, characteristic for the anti-parallel structures, has been detected, suggesting that the peptides in the cylindrical micelles form parallel β-sheets—consistent with a model based on TEM data. Amide A stretching band maximum in all spectra studied appears around 3280 $cm^{-1}$, indicating a high level of hydrogen bonding in the PA supramolecular assemblies.

Figure 15A:
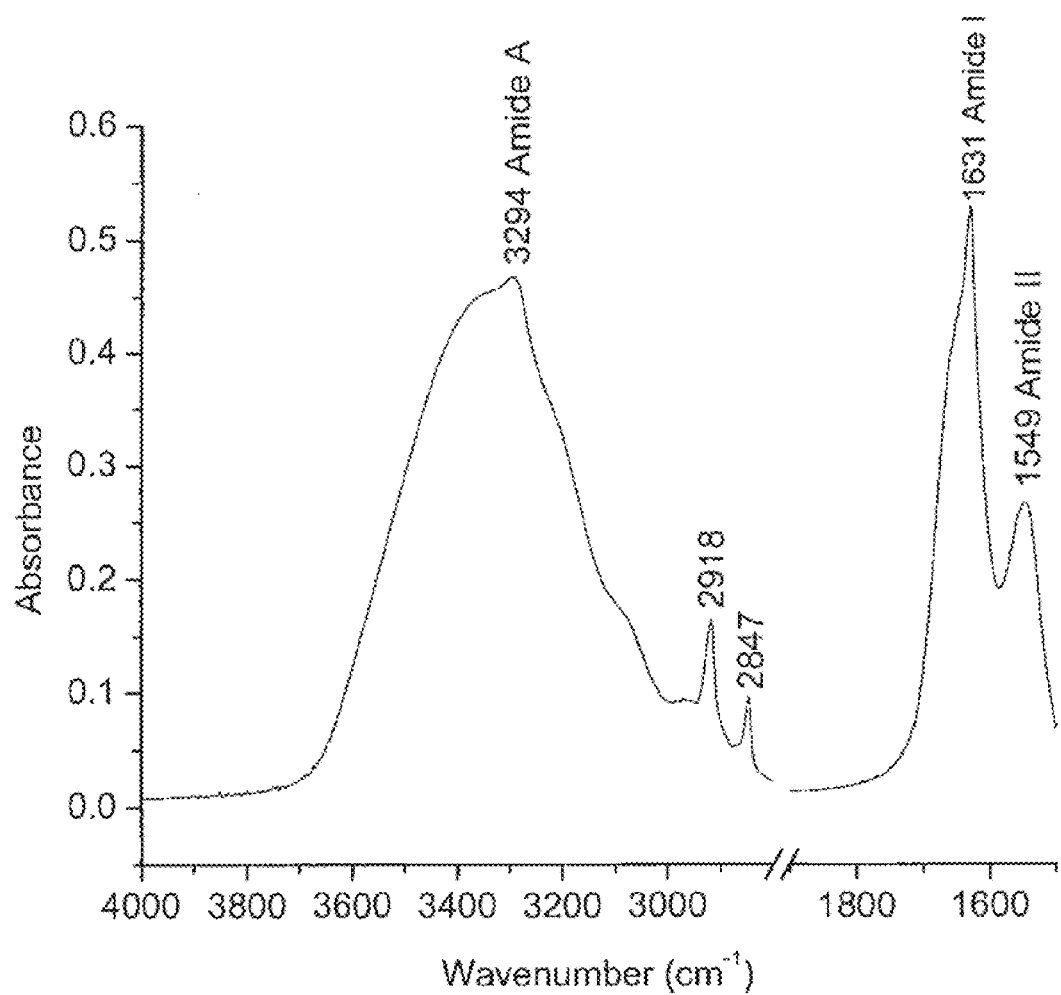
FIGS. 15A-C. FT-IR spectra of the peptide-amphiphile gels. A. The fragment of the spectrum of $CaCl_2$ induced gel of the molecule 27, showing the regions of Amide A, Amide I and Amide II bands. B. The Amide I and II region of the normalized spectra of the gels of the molecule 27 assembled by addition of $CaCl_2$ and at low pH. C. The Amide I and II region of the normalized spectra of the gels of the molecule 32 assembled by addition of $CaCl_2$, pH and KCl.
Figure 15B:
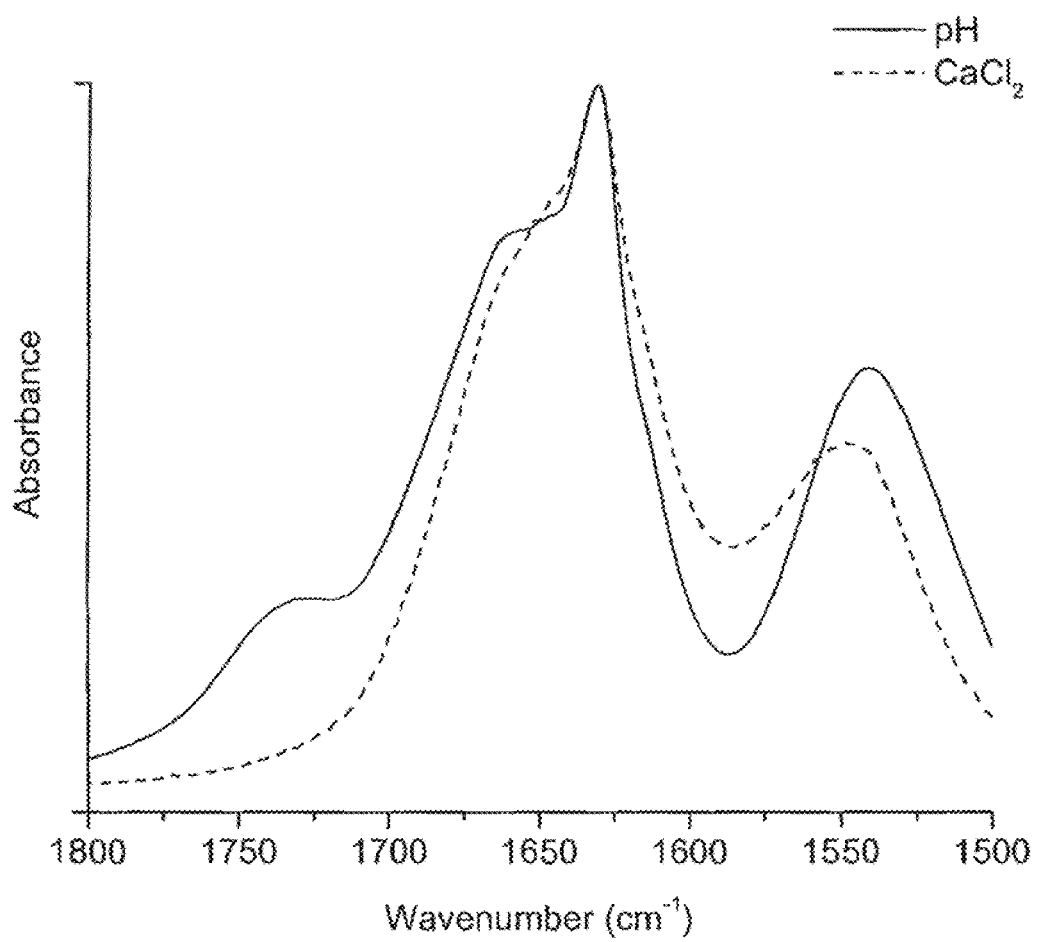
Figure 15C:
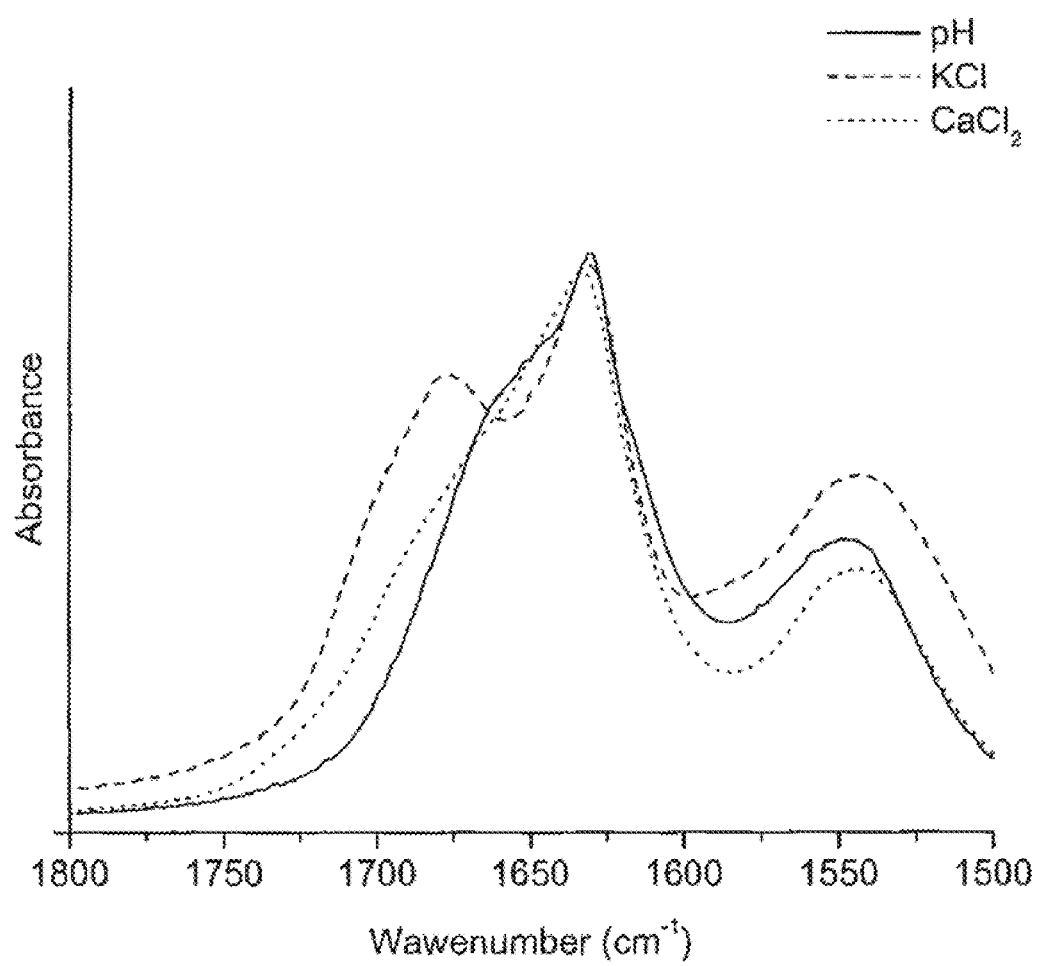

The spectra of the PA gels formed by pH induced self-assembly contain a peak in the 1720-1750 cm−1 region—characteristic of C=O stretching of non ionized carboxyls. In contrast, no evident peak has been detected in this region in the spectra of the polyvalent metal ion induced gels. It has been reported in the literature that the formation of the metal carboxyl complexes of amino acids results in a low frequency shift of this band maximum to the 1560 $cm^{-1}$-1610 $cm^{-1}$ region. No such peaks were observed in this region in the spectra of ion induced PA supramolecular assemblies, which may be due to the overlap between this peak and neighboring Amide I and Amide II bands. However the fact that the minima between Amide I and Amide II peaks is deeper in the spectra of pH induced self-assemblies compare to ion induced self-assemblies suggests presence of the peak in this region. (Reference is made to FIG. 15.)

Example 23b

For FT-IR studies the gels were quick frozen in liquid N2 and lyophilized. The KBr pellets of the lyophilized gels were analyzed on an FT-IR Biorad spectrometer. 32 scans per spectrum were taken at resolution 2 cm−1. The spectra were analyzed using Origin 6.0 program.

Example 24

The synthesis of the peptide amphiphiles illustrates in examples 19-22 was performed using a standard synthesis scheme described elsewhere, herein, and as further available in the literature. Regarding gelation and with reference to the data of Table 3, 200 μm volumes of PA solutions at concentrations 10 mg/ml (approximately 8 mM), pH 7.5 were mixed with 1 M solutions of NaCl, KCl, $MgCl_2$, $CaCl_2$, $BaCl_2$, $ZnBr_2$, $CdCl_3$, Ge and $Cu(ClO_4)_2$. The amount of polyvalent ions added to the solutions varied from 0.5 to 5 metal ions per molecule of PA. For monovalent metal ions the maximum concentration of 6 M of metal ions per 10 mM of PA molecules has been tested. The solutions of the metal salts were added to the PA solutions by micropeppetors, the solutions were stirred briefly, in order to obtain better mixing of the components. The formation of self-supporting gels was examined by flipping of the vials up side down. In order to test the ability of cell compatible solutions to induce a gelation of PAs equal amounts 10 mM PA solutions were mixed with following formulations: MEM-α, DMEM containing 10% of fetal bovine serum, PBS without $Ca^{+2}$ and $Mg^{+2}$ and Hank's solution without $Ca^{+2}$ and $Mg^{+2}$ (Gibco). The ability of the above solutions to induce formation of the PAs was examined visually by flipping the vials up side down.

Various other amphiphile compositions of this invention can be prepared in analogous fashion, as would be known to those skilled in the art and aware thereof, using known procedures and synthetic techniques or straight-forward modifications thereof depending upon a desired amphiphile composition or peptide sequence.

As demonstrated by the preceding examples, figures and data, the fact that the hydroxyapatite crystals grow on the bundles of fibers with their c-axes oriented along the long axes of the micelles could be of interest for design of new materials for mineralized tissue repair. This nanoscale organization resembles that of hydroxyapatite crystals in mineralized ECM in which the HA crystals also grow in parallel arrays with their c-axes co-aligned with long axes of the organic fibers (W. Traub, S. Weiner, *Proc. Nat. Acad. Sci.* 86, 9822-9826 (1989)). This arrangement is the most important characteristic of the biominerals belonging to the bone family (S. Weiner, H. D. Wagner, *Annu. Rev. Mater. Sci.* 28, 271-298 (1998)). The organization of the collagen fibers, porosity, mineral-organic ratio vary in different members of this family, yet all of them are built from the collagen fibrils containing parallel arrays of hydroxyapatite crystals (W. Traub, S. Weiner, *Proc. Nat. Acad. Sci.* 86, 9822-9826 (1989); S. Weiner, W. Traub, *FASEB J.* 6, 879-885 (1992); W. J. Landis, K. J. Hodgens, J. Arena, M. J. Song, B. F. McEwen, *Microsc. Res. Techniq.* 33, 192-202 (1996)).

It has been proposed that in the case of the pH triggered self-assembly cylindrical micelles form due to the protonation of acidic groups of the peptide and reduction of the repulsive forces between molecules—that in the case of pH triggered self-assembly of the PAs the major driving force is hydrophobic interactions between the aliphatic tails of the molecules, rather the interactions between the peptide segments. The results reported herein show that the interactions between peptide segments of the PA via metal bridges or due to amphiphilicity of the sequence, may also play a role in the self-assembly. Gelation under physiological conditions demonstrate such PAs as potentially important materials for biomedical applications, such as tissue engineering or delivery of cells, drugs or other therapeutic agents. Supramolecular assemblies induced by addition of metal ions are stable in wide pH range and provide as potential applications embedding cells in a gel or in situ gelation of a tissue repair material.

While the principles of this invention have been described in connection with specific embodiments, it should be understood clearly that these descriptions are added only by way of example and are not intended to limit, in any way, the scope of this invention. For instance, various peptide amphiphiles have been described in conjunction with specific residues and corresponding cell adhesion, but other residues can be used herewith to promote a particular cell adhesion and tissue growth on the nanostructures prepared therefrom. Likewise, while the present invention has been described as applicable to biomimetic material or tissue engineering, it is also contemplated that gels or related systems of such peptide amphiphiles can be used as a delivery platform or carrier for drugs, cells or other cellular or therapeutic material incorporated therein. Other advantages and features will become apparent from the claims filed hereafter, with the scope of such claims to be determined by their reasonable equivalents, as would be understood by those skilled in the art.

What is claimed:

1. A method of making a cylindrical micellar nanofiber composed of beta-sheets of peptide segment of peptide amphiphile comprising the steps of:

(a) providing the peptide amphiphile molecule in an aqueous solution, wherein said peptide amphiphile molecule comprises a single $C_6$ to $C_{22}$ linear hydrocarbon segment covalently linked to a peptide segment comprising a bioactive epitope sequence selected from RGD, KGE, IKVAV (SEQ ID NO: 1) and YIGSR (SEQ ID NO: 20); and (b) contacting said peptide amphiphile molecule with an effective amount of a metal ion sufficient to induce formation of a cylindrical micellar nanofiber composed of beta-sheets.

2. The method of claim 1, wherein said contacting step occurs under physiological conditions.

3. The method of claim 1, wherein said metal ion is present in a bodily fluid.

4. The method of claim 1, wherein the metal ion selected from the group consisting of $Ca^{2+}$, $Mg^{2+}$, $Cd^{2+}$, $Fe^{2+}$ and $Zn^{2+}$ divalent ions, $Al^{3+}$, $Fe^{3+}$, and $Gd^{3+}$ trivalent ions, and combination of said ions.

5. The method of claim 1, wherein said peptide amphiphile molecule has a net charge at substantially physiological pH.

6. The method of claim 1, wherein said peptide segment further comprises at least one phosphorylated residue.

7. The method of claim 6, wherein said phosphorylated residue is phosphoserine.

8. The method of claim 1, wherein said peptide segment further comprises a residue with a functional moiety capable of intermolecular covalent bond formation.

9. The method of claim 8, wherein said residue is cysteine.

10. The method of claim 9, wherein said peptide segment further comprises at least one phosphoserine residue.

11. The method of claim 10, wherein said peptide segment further comprises at least one glycine residue between said cysteine and phosphoserine residues.

12. The method of claim 1, wherein said peptide segment comprises a first peptide sequence selected from the group consisting of CCCCGGGS(p) (SEQ ID NO: 3), CCCCGGGS (SEQ ID NO: 26), CCCCGGGE (SEQ ID NO: 27), AAAAGGGS(p) (SEQ ID NO: 28), AAAAGGGS (SEQ ID NO: 29), GGGS(p) (SEQ ID NO: 30), and GGGS (SEQ ID NO: 31) and a second peptide sequence selected from RGD, KGE, IKVAV (SEQ ID NO: 1) and YIGSR (SEQ ID NO: 20), wherein S(p) stands for phosphorylated serine residue.

13. The method of claim 1, wherein said hydrocarbon segment is linked to the N-terminus of said peptide segment.

14. The method of claim 1, wherein said cylindrical micellar nanofiber has dimensional and functional characteristics mimetic of collagen fibrils.

15. The method of claim 1, wherein said cylindrical micellar nanofiber forms a conical shape comprised of a narrow hydrocarbon tail at one end and a bulkier peptide region at the other.

16. The method of claim 1, wherein said cylindrical micellar nanofiber displays a secondary structure that includes both beta-sheets and alpha-helices.

* * * * *